US012724782B2

(12) United States Patent
Ruehle

(10) Patent No.: US 12,724,782 B2
(45) **Date of Patent: *Sep. 1, 2026**

(54) FLEXIBLE SEED EXTENSION FOR HASH TABLE GENOMIC MAPPING

(71) Applicant: Illumina, Inc., San Diego, CA (US)

(72) Inventor: Michael Ruehle, Fort Worth, TX (US)

(73) Assignee: Illumina, Inc., San Diego, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 18/497,830

(22) Filed: Oct. 30, 2023

(65) Prior Publication Data

US 2024/0061843 A1 Feb. 22, 2024

Related U.S. Application Data

(63) Continuation of application No. 16/882,158, filed on May 22, 2020, now Pat. No. 11,803,554.

(Continued)

(51) Int. Cl.

*G06F 16/2455* (2019.01)
*G06F 16/22* (2019.01)
*G16B 30/10* (2019.01)

(52) U.S. Cl.

CPC .... *G06F 16/24566* (2019.01); *G06F 16/2282* (2019.01); *G16B 30/10* (2019.02)

(58) Field of Classification Search

CPC ........... G06F 16/24566; G06F 16/2282; G16B 30/10

See application file for complete search history.

(56) References Cited

U.S. PATENT DOCUMENTS 10,083,276 B2 9/2018 Van Rooyen et al.
2014/0288851 A1 9/2014 Park et al.

(Continued)

FOREIGN PATENT DOCUMENTS

AU 2016287752 2/2018
AU 2016287752 B2 * 12/2021 ............ G16B 30/20

(Continued)

OTHER PUBLICATIONS

Buckingham et al., "Locality-Sensitive Hashing for Protein Classification," AusDM, Oct. 2014, 141-7.

(Continued)

*Primary Examiner* — Khanh B Pham
*Assistant Examiner* — Faezeh Forouharnejad
(74) *Attorney, Agent, or Firm* — Heslin Rothenberg Farley & Mesiti P.C.

(57) ABSTRACT

Methods, systems, and apparatuses, including computer programs for generating and using a hash table configured to improve mapping of reads are disclosed that include obtaining a first seed of K nucleotides from a reference sequence, generating a seed extension tree having a nodes, wherein each node of the nodes corresponds to (i) an extended seed that is an extension of the first seed and has a nucleotide length of K* and (ii) one or more locations, in a seed extension table, that include data describing reference sequence locations that match the extended seed, and for each node: storing interval information at a location of the hash table that corresponds to an index key for the extended seed, wherein the interval information references one or more locations in the seed extension table that include reference sequence locations that match the extended seed associated with the node.

22 Claims, 8 Drawing Sheets

Related U.S. Application Data

(60) Provisional application No. 62/852,965, filed on May 24, 2019.

(56) References Cited

U.S. PATENT DOCUMENTS

| | | | |
|---|---|---|---|
| 2016/0306923 | A1 | 10/2016 | Van Rooyen et al. |
| 2020/0372031 | A1 | 11/2020 | Ruehle |

FOREIGN PATENT DOCUMENTS

| | | | |
|---|---|---|---|
| CN | 105243297 | A | 1/2016 |
| CN | 106295250 | | 1/2017 |
| CN | 109326325 | A | 2/2019 |
| JP | 2012-032975 | A | 2/2012 |
| JP | 2013-106567 | A | 6/2013 |
| JP | 2019-510323 | A | 4/2019 |
| RU | 2200762 | | 3/2003 |
| WO | WO 2016/141294 | | 9/2016 |
| WO | WO 2017/004589 | | 1/2017 |
| WO | WO 2018/068014 | | 4/2018 |

OTHER PUBLICATIONS

CA Office Action in Canadian Appln. No. 3,104,546, mailed on Dec. 15, 2024, 8 pages.

Duan et al., "Ultrascalable Read Mapping on Sunway Taibu Light.," 2017 IEEE International Conference on Cluster Computing (CLUSTER), Sep. 5, 2017, 36-46.

Georganas et al., "meraligner: A fully parallel sequence aligner," 2015 IEEE International Parallel and Distributed Processing Symposium, May 25, 2015 May 25, 561-70.

IL Office Action in Israeli Appln. No. 279558, dated May 14, 2023, 7 pages (with English translation).

Illumina DRAGEN Bio-IT Platform v3.2.8 1-75 User Guide 11, Apr. 29, 2019, retrieved online Sep. 29, 2020, from URL <https://support.illumina.com/content/dam/illumina-support/documents/documentation/software_documentation/dragen-bio-it/dragen-bio-it-platform-v3.2.8-user-guide-1000000085871-00.pdf>, 124 pages.

IN Office Action in Indian Appln. No. 202017055684, mailed on Mar. 6, 2024, 5 pages.

Miller et al., "A 26-hour system of highly sensitive whole genome sequencing for emergency management of genetic diseases," Genome Medicine, Dec. 2015, 7(1):1-6.

PCT International Search Report and Written Opinion in International Appln. No. PCT/US2020/034395, dated Sep. 14, 2020.

RU Office Action in Russian Appln. No. 2020142536, dated Oct. 26, 2022, 21 pages (with English translation).

SG Office Action in Singaporean Appln. No. 11202012439S, mailed on Jan. 30, 2024, 9 pages.

US Non-Final Office Action in U.S. Appl. No. 16/667,642, dated Sep. 29, 2022, 18 pages.

AU Office Action in Australian Appln. No. 2020285655, mailed on Jan. 29, 2025, 3 pages.

CA Office Action in Canadian Appln. No. 3,104,546, mailed on Dec. 15, 2023, 8 pages.

CN Office Action in Chinese Appln. No. 202080003658.1, mailed on Feb. 29, 2024, 18 pages (with English translation).

CN Office Action in Chinese Appln. No. 202080003658.1, mailed on Jul. 17, 2024, 9 pages (with English translation).

EP Extended European Search Report in European Appln. No. 24183260.9, mailed on Dec. 11, 2024, 12 pages.

JP Office Action in Japanese Appln. No. 2020-572747, mailed on Jul. 29, 2024, 14 pages (with English translation).

PCT International Preliminary Report on Patentability in International Appln. No. PCT/US2020/034395, dated Dec. 2, 2021, 15 pages.

US Final Office Action in U.S. Appl. No. 16/882,158, mailed on Feb. 1, 2023, 30 pages.

US Non-Final Office Action in U.S. Appl. No. 16/882,158, mailed on Aug. 10, 2022, 29 pages.

* cited by examiner

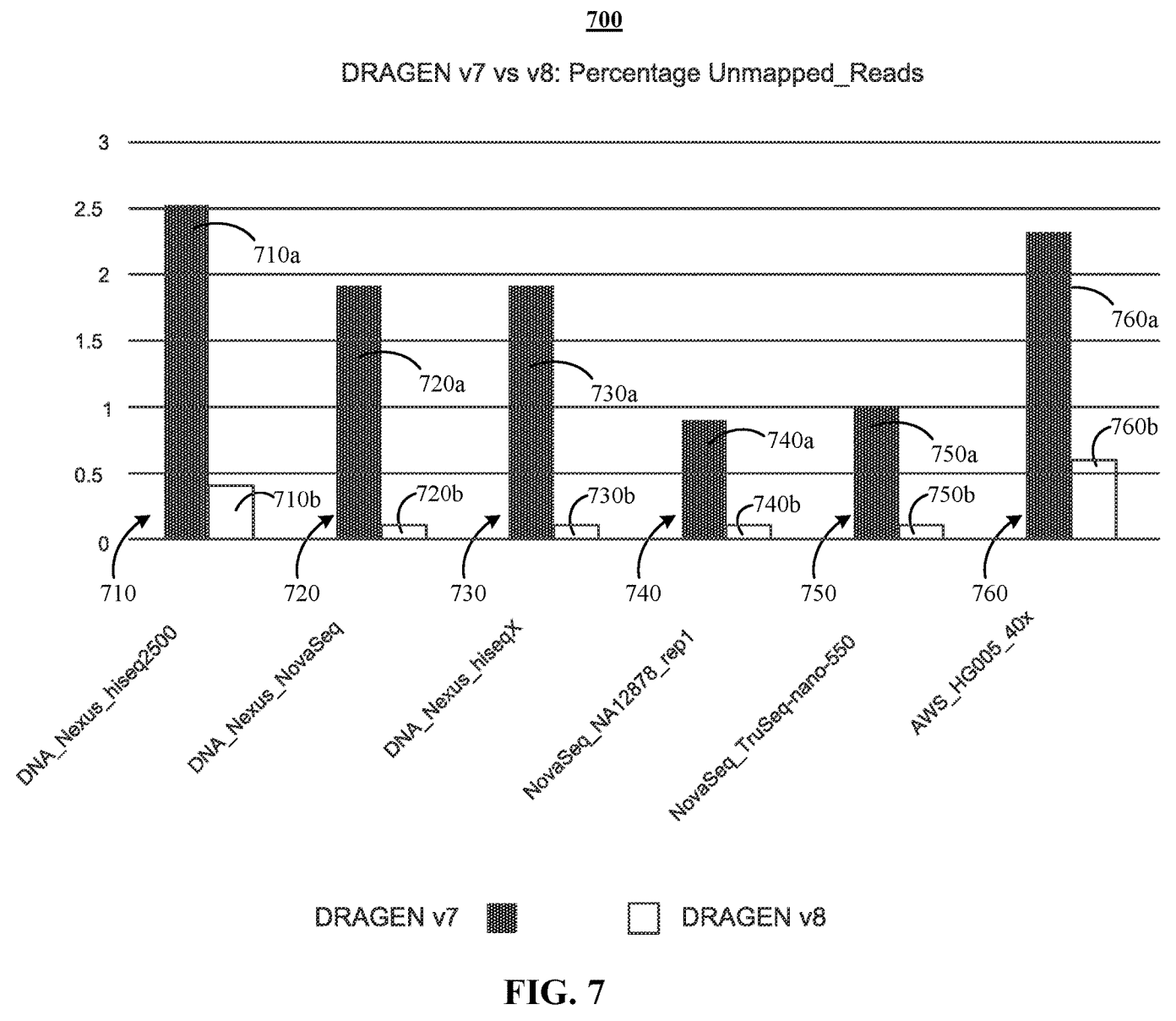

700

DRAGEN v7 vs v8: Percentage Unmapped_Reads 3
2.5
2
1.5
1
0.5
0

710a
710b
720a
720b
730a
730b
740a
740b
750a
750b
760a
760b

710 DNA_Nexus_hiseq2500
720 DNA_Nexus_NovaSeq
730 DNA_Nexus_hiseqx
740 NovaSeq_NA12878_rep1
750 NovaSeq_TruSeq-nano-550
760 AWS_HG005_40x DRAGEN v7
DRAGEN v8

FIG. 7

FLEXIBLE SEED EXTENSION FOR HASH TABLE GENOMIC MAPPING

CROSS-REFERENCE TO RELATED APPLICATION

This application is a continuation application of U.S. patent application Ser. No. 16/882,158 filed May 22, 2020, which claims the benefit of U.S. Provisional Patent Application No. 62/852,965 filed on May 24, 2019, which is incorporated herein by reference in its entirety.

BACKGROUND

A nucleic acid sequencer is an instrument that is configured to automate the process of nucleic acid sequencing. Nucleic acid sequencing is a process of determining an order of nucleotides in a nucleic acid sequence. Nucleic acids may include deoxyribonucleic acid (DNA) or ribonucleic acid (RNA).

The nucleic acid sequencer is configured to receive a nucleic acid sample and generate output data, referred to as one or more "reads," that represents an order of nucleotides in the nucleic acid sample. The nucleotides in a DNA sample can include one or more nucleotide bases that include guanine (G), cytosine (C), adenine (A), and thymine (T) in any combination. The nucleotides in a RNA sample can include one or more bases that include G, C, A, and uracil (U) in any combination.

The reads generated by the DNA sequencer can be mapped to a known sequence of nucleotides of a reference genome using a mapping and aligning engine. The mapping of the reads to the sequence of nucleotides of the reference genome can be achieved by a mapping and aligning engine using a hash table index.

SUMMARY

The present disclosure describes construction and use of a hash table index that facilitates flexible seed extension to improve the performance of genomic mapping and aligning systems. In particular, the present disclosure can be used to perform flexible seed extension in a manner that (i) reduces expenditure of computational resources and power and (ii) solves problems with conventional seed extension methods described herein. To achieve these advantages, the present disclosure provides, inter alia, an "interval record" that can be stored in a hash table location.

Aspects of the present disclosure enable a mapping and aligning unit to use an interval record alone, or in conjunction with one or more extend records, to reduce the number of matching locations to be processed by the mapping and aligning unit through seed extension while also providing the mapping and aligning unit flexibility in determining whether matching reference locations identified using dynamic seed extension are accurate or, in some instances, whether seed extension using one or more extend records should even occur. This results in a mapping and aligning unit that uses less power and fewer computational resources while also being more accurate than other mapping and aligning units that avail themselves of the conventional seed extension techniques.

In one aspect, the present disclosure provides methods for generating a hash table for mapping of sample reads to a reference. In one aspect, the methods can include actions of obtaining, by a computer system, a first seed of nucleotides from a reference sequence, wherein the first seed has a length of K nucleotides, determining, by the computer system, that the first seed matches more than a predetermined number of reference sequence locations, based on determining that the first seed matches more than a predetermined number of reference sequence locations, generating, by the computer system, a seed extension tree having a plurality of nodes, wherein each node of the plurality of nodes corresponds to (i) an extended seed that is an extension of the first seed and has a nucleotide length of K*, wherein K* is one or more nucleotides greater than K, and (ii) one or more locations, in a seed extension table, that include data describing reference sequence locations that match the extended seed, and for each node of the plurality of nodes: storing, by the computer system, interval information at a location of the hash table that corresponds to an index key for the extended seed, wherein the interval information references one or more locations in the seed extension table that include data describing reference sequence locations that match the extended seed associated with the node.

Other aspects include corresponding systems, apparatus, and computer programs to perform the actions of methods as disclosed herein as defined by instructions encoded on computer readable storage devices.

These and other aspects may optionally include one or more of the following features. For instance, in some implementations, each of the matching reference sequence locations include the K nucleotides of the first seed.

In some implementations, the methods can further include obtaining, by the computer system, a second seed of nucleotides from the reference sequence that is different than the first seed, determining, by the computer system, that the second seed does not match more than the predetermined number of reference sequence locations, and based on determining, by the computer system, that the second seed does not match more than the predetermined number of reference sequence locations: obtaining, by the computer system, data describing each of the reference sequence locations that match the second seed, and storing, by the computer system, the data describing the reference sequence locations that match the second seed at a second location of the hash table that corresponds to an index key for the second seed.

In some implementations, the one or more locations in the seed extension table that include data describing reference sequence locations that match the extended seed can include a contiguous interval of locations in the seed extension table that include data describing reference sequence locations that match the extended seed.

In some implementations, the one or more locations in the seed extension table that include data describing reference sequence locations that match the extended seed associated with the node can include a contiguous interval in an extension table of reference sequence locations that match the extended seed associated with the node.

In some implementations, obtaining, by a computer system, a first seed of nucleotides from a reference sequence, the first seed representing a sequence of nucleotides having a nucleotide length of K nucleotides can include determining, by the computer system, a location of a seed access window within a reference sequence, and obtaining, by the computer system, a subset of the reference sequence that is identified by the seed access window.

In some implementations, the methods can further include adjusting, by the computer system, the seed extension window K nucleotides forward along the reference sequence to identify a second seed of nucleotides from the reference sequence having a nucleotide length of K nucleotides, obtaining, by the computer system, the second seed from the reference sequence, determining, by the computer system, that the second seed matches more than a predetermined number of reference sequence locations, based on determining that the second seed matches more than a predetermined number of reference sequence locations, generating, by the computer system, a second seed extension tree having a plurality of second nodes, wherein each second node of the plurality of second nodes corresponds to (i) a second extended seed that is an extension of the second seed and has a nucleotide length of K*, wherein K* is one or more nucleotides greater than K, and (ii) a second one or more locations, in a second seed extension table, that includes data describing reference sequence locations that match the second extended seed, and for each second node of the plurality of second nodes: storing, by the computer system, second interval information at a location of the hash table that corresponds to an index key for the second extended seed, wherein the second interval information references one or more locations in the second seed extension table that include data describing reference sequence locations that match the second extended seed associated with the second node.

In some implementations, the methods can further include for each node of the plurality of nodes: determining, by the computer system, whether the node of the seed extension tree is a leaf node, and based on determining, by the computer system, that the node of the extension tree is not a leaf node, storing, by the computer system, an extend record in the location of the hash table that corresponds to the index key for the extended seed.

In some implementations, the extend record includes one or more instructions that, when executed by the computer system, cause the computer system to add one or more additional nucleotides to a seed associated with the extend record.

In some implementations, the methods can further include based on determining, by the computer system, that the node extension tree is a leaf node, determining, by the computer system, not to store an extend record in the location of the hash table that corresponds to the index key for the extended seed.

In some implementations, the methods can further include generating, by the computer system, the seed extension table. In such implementations, generating the seed extension table can include identifying, by the computer system, each seed of the reference sequence that matches the first seed, and storing, by the computer system, data identifying the identified seeds in the seed extension table.

In some implementations, the methods can further include sorting, by the computer system, the identified seeds in the seed extension table.

In some implementations, the methods can further include generating, by the computer system, a hash table installation package, the hash table installation package including instructions that, when processed by one or more computers that receive the hash table installation package, cause the one or more computers to install the hash table in a memory that is accessible by a programmable logic circuit.

In some implementations, the hash table installation package can include the seed extension table, and the hash table installation package can include instructions to instruct (i) the programmable logic circuit or (ii) another computer, to store the seed extension table in a memory device that is accessible to the programmable logic circuit.

In some implementations, providing, by the computer system, the hash table installation package to another computer.

In some implementations, the other computer can include (i) a computer that is configured to communicate with the programmable logic circuit or (ii) the programmable logic circuit itself.

In some implementations, the computer system can include a plurality of computers.

In another aspect, the present disclosure provides methods for using a hash table to improve the mapping of sample reads to a reference sequence. In one aspect, the methods can include executing, by a mapping and aligning unit, a query of a hash table, the query including a first seed, wherein the first seed includes a subset of nucleotides that were obtained from a particular read of the sample reads, obtaining, by the mapping and aligning unit, a response to the executed query that includes information stored by a location of the hash table that is determined to be responsive to the query, determining, by the mapping and aligning unit, whether the response to the executed query includes (i) an extend record (ii) an interval record, or (iii) one or more matching reference sequence locations, based on determining, by the mapping and aligning unit, that the response to the executed query includes (i) an extend record and (ii) an interval record: determining, by the mapping and aligning unit, whether an extension table is to be accessed to obtain one or more matching reference sequence locations in the extension table that are referenced by the interval record, based on determining that the extension table is not to be accessed: determining, by the mapping and aligning unit, whether to store the first information describing the interval record in a memory device as information describing a candidate best interval, generating, by the mapping and aligning unit, a first extended seed that is an extension of the first seed using the extend record, generating, by the mapping and aligning unit, a subsequent hash query that includes the first extended seed, and executing, by the mapping and aligning unit, the subsequent hash query of the hash table.

Other versions include corresponding systems, apparatus, and computer programs to perform the actions of methods defined by instructions encoded on computer readable storage devices.

These and other aspects of the disclosure can optionally include one or more of the following features. For instance, in some implementations, the methods can further include based on determining that the extension table is to be accessed: accessing, by the mapping and aligning unit, the extension table to obtain the one or more matching reference sequence locations in the extension table that are referenced by the interval record, and adding, by the mapping and aligning unit, the one or more matching reference sequence locations to a seed match set.

In some implementations, the methods can further include determining, by the mapping and aligning unit, that the response to the executed query includes one or more matching reference sequence locations, and based on determining, by the mapping and aligning unit, that the response to the executed query includes one or more matching reference sequence locations: adding, by the mapping and aligning unit, the one or more matching reference sequence locations to a seed match set.

In some implementations, determining, by the mapping and aligning unit, whether to store the first information describing the interval record in a memory device as information describing a candidate best interval can include determining, by the mapping and aligning unit, that there is not prior information describing an interval record as a candidate best interval for the particular read, and storing, by the mapping and aligning unit, the first information describing the interval record in the memory device as information describing a candidate best interval.

In some implementations, the methods can further include obtaining, by the mapping and aligning unit, a response to the subsequent executed query that includes information stored by a location of the hash table that is determined to be responsive to the query, determining, by the mapping and aligning unit, whether the response to the subsequent executed query includes (i) a second extend record (ii) a second interval record, or (iii) one or more matching reference sequence locations, based on determining, by the mapping and aligning unit, that the response to the subsequent executed query includes (i) the second extend record or (ii) the second interval record: determining, by the mapping and aligning unit, whether an extension table is to be accessed to obtain one or more matching reference sequence locations in the extension table that are referenced by the second interval record, based on determining that the extension table is not to be accessed: determining, by the mapping and aligning unit and using one or more heuristic rules, whether the second information describing the second interval record or the first information describing the candidate best interval is to be used as the candidate best interval, generating, by the mapping and aligning unit, a second extended seed that is an extension of the first extended seed using the second extend record, generating, by the mapping and aligning unit, a third hash query that includes the second extended seed, and executing, by the mapping and aligning unit, the third query of the hash table that includes the second extended seed.

In some implementations, determining, by the mapping and aligning unit and using one or more heuristic rules, whether the second information describing the second interval record or the first information describing the candidate best interval is to be used as the best interval can include selecting either the second information describing the second interval record or the first information describing the candidate best interval record based on a plurality of factors that include (i) a number of matching reference sequence locations returned by each of the interval record and the second interval record, (ii) a predetermined threshold level of reference sequence locations, or (iii) each seed length of the respective seeds that reached the hash locations storing the interval record and the second interval record.

In some implementations, the interval record references a plurality of locations, in the seed extension table, that include data describing reference sequence locations that match the first seed of the query.

In some implementations, the plurality of locations, in the seed extension table, that include data describing reference sequence locations that match the first seed of the query can include a contiguous interval, in an extension table, of reference sequence locations that match the first seed of the query.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

These and other aspects of the present disclosure are discussed in more detail in the detailed description below with reference to the accompanying drawings and the claims.

BRIEF DESCRIPTION OF THE DRAWINGS

FIG. 7 is an illustration of a bar graph displaying data representing test results in the form of a percentage of unmapped reads in a system using a flexible seed extension method as described herein compared with a system not using a flexible seed extension method.

DETAILED DESCRIPTION

Figure 1:
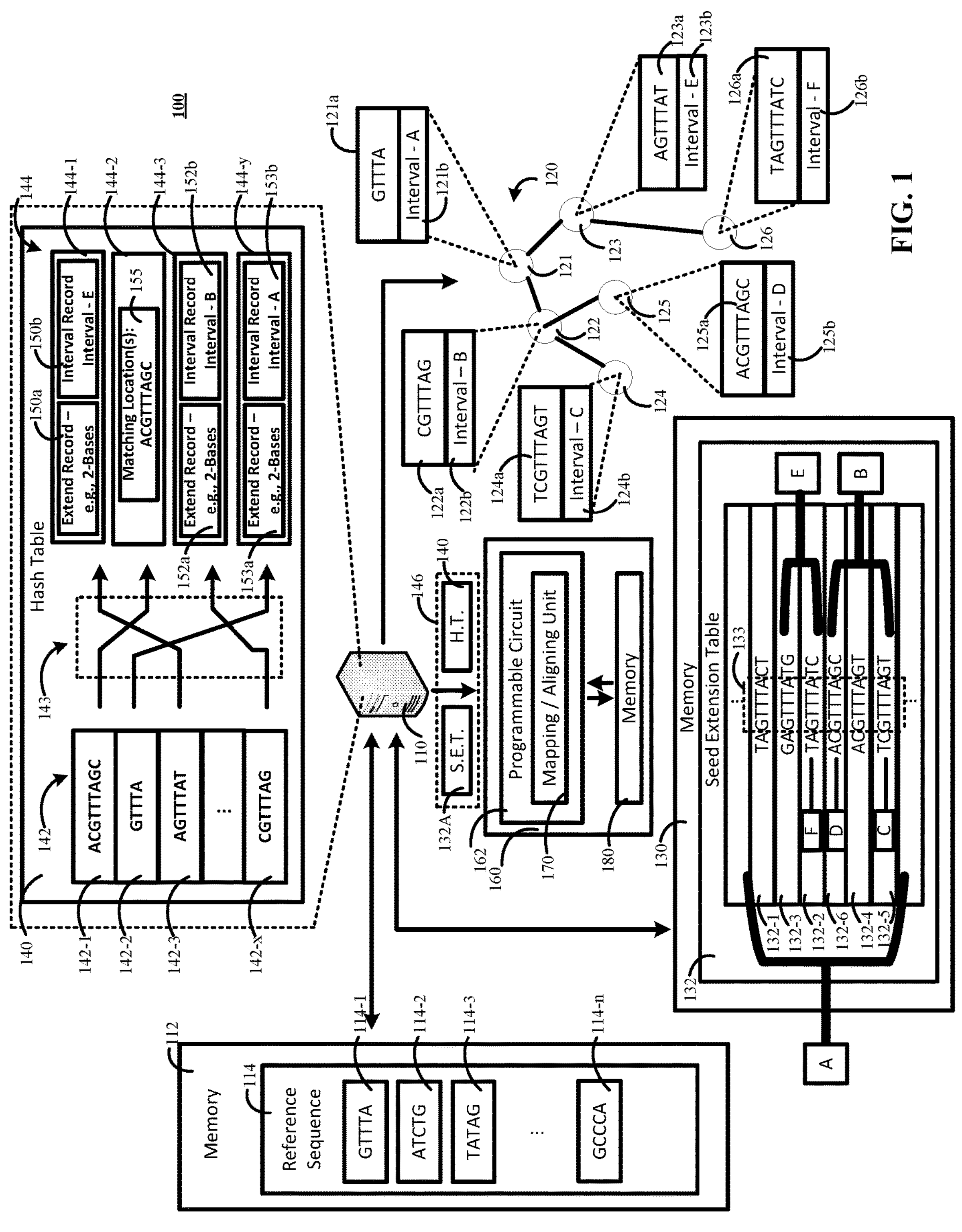
FIG. 1 is a contextual diagram of a system for generating a hash table index that facilitates flexible seed extension for hash table genomic mapping.

The present disclosure describes construction and use of a hash table index that facilitates flexible seed extension to improve the performance of genomic mapping and aligning systems. As used herein, the term "seed" refers to a subset of sequential nucleotides that exists in a nucleic acid read ("read") or a nucleic acid reference sequence ("reference sequence"). By way of example, a short seed for a read can have, for example, 21 bases or nucleotides that are extracted from a read of, for example, 150 bases or nucleotides generated by a nucleic acid sequencer ("sequencer") based on a biological sample input into the sequencer. Such short seeds can match hundreds, thousands, hundreds of thousands, or even more, locations of a reference sequence. Seeds of a reference sequence can include a subset of sequential nucleotides from a reference sequence that represents a reference sequence location. Identification of such large quantities of reference sequence locations that match a particular short seed of a read can occur for multiple reasons including the occurrence of repetitive sequences such as ". . . ATATAT . . . ," which may occur in many locations in a reference sequence. Alternatively, or in addition, such large quantities of matching reference sequence locations can occur, because many near-copies of a genomic sequence can appear in a reference sequence.

These large quantities of reference sequence locations that match a particular short seed can cause strain on conventional mapping and aligning units using conventional hash table indices, as the mapping and aligning engines can be forced to process large quantities of matches. Such excess processing of large quantities of reference sequence locations that match a particular short seed results in unnecessary expenditures of computational resources including a taxing of processing resources, memory resources, and a waste of power used to power the processing resources, the memory devices, and cooling units, which are used to cool the processing resources and memory resources, or any combination thereof.

Conventional methods have been employed to address problems that can arise from the identification and processing of large quantities of reference sequence locations that match a short seed. For example, conventional methods have been employed that use extend records stored in hash table locations to extend a short seed iteratively. Such methods include those described by, for example, U.S. Pat. No. 10,083,276, which is herein incorporated by reference, that can return an "extend record" stored in a location of the hash table that corresponds to a seed of a hash query. The extend record can be used to create an extended seed by symmetrically increasing the length of the seed in the received hash query by adding one or more bases or nucleotides on each end of seed. The conventional systems can then use another hash query that includes the extended seed to query the hash table again. This other hash query, having the extended seed, is likely to correspond to a hash location identifying fewer reference locations that match the extended seed because the extended seed is longer. This iterative process can continue until (i) a resulting match set shrinks enough to include less than a threshold number of reference sequence locations that match the extended seed, (ii) the match set becomes empty, (iii) a maximum seed extension is reached, or (iv) a next extension is not possible because the extension would move beyond an edge of the read upon which the short seed is based. Critically, in a conventional system, the mapping and aligning unit may only be able to obtain a nonempty set of matching reference locations if the iterative process terminates in manner (i) above, not if it terminates in any of manners (ii), (iii), or (iv), above.

These conventional methods can help to reduce the quantity of reference sequence locations that match a short seed. However, these conventional methods suffer from three distinct problems.

First, conventional methods can be susceptible to the "unmapped read problem." The unmapped read problem occurs when conventional seed extension methods return zero matches for an extended seed. Such zero match results sets can occur if the extended seed incorporates a variant such as an SNP or if the extended seed overruns the edge of a read to which the extended seed corresponds. If such a scenario occurred for each seed position of a read using conventional methods, the read may be unmapped.

Second, conventional methods can be susceptible to the "high-confidence mismapping problem." Such high-confidence mismapping problems occur when the extended seed includes a variant such as an SNP but still matches one or more reference locations. Such mappings can be characterized by a high-confidence score such as a high MAPQ score even though the extended seed is incorrectly mapped. If this happens for each seed position of a read using conventional methods, then the read may be mismapped, potentially with high confidence. For such mappings, evidence to the contrary can be missing. High-confidence mismappings can be more damaging to overall mapper accuracy than low-confidence mismappings. A MAPQ score can include a quality score that quantifies a probability that a mapped read is misplaced.

Third, the conventional methods can be susceptible to the "fixed maximum matches problem." Generally, hash tables constructed for seed extension use a maximum match parameter M such as M=16. This parameter ensures that no leaf node of a seed extension tree exceeds the parameter of M. However, some applications can benefit from using a different maximum match parameter M* such as M=64. Conventional seed extension methods would continue to extend the seed iteratively until the leaf node is reached. Accordingly, an application using conventional methods could not stop extension of the seeds when a matching set of M=64 is reached unless the hash table was rebuilt such that the maximum match parameter M was set to 64.

Innovative aspects of the present disclosure can be used to perform flexible seed extension in a manner that (i) reduces expenditure of computational resources and power as described herein and (ii) solves problems with conventional seed extension methods such as those problems described above. To achieve these advantages, the present disclosure provides, inter alia, an "interval record" that can be stored in a hash table location. The interval record identifies, for a particular seed, a contiguous set of reference sequence locations, stored in a seed extension table, that match the particular seed. Upon execution of a hash query identifying a particular seed, the mapping and aligning unit can determine, based on the contents of a hash location that is responsive to the query, whether to (i) extend a seed based on a seed extend record stored at the hash location, (ii) store an interval record that identifies reference locations, in a seed extension table, that match the particular seed, or (iii) access reference sequence locations, in a seed extension table, identified by an interval record stored at the hash location. In some implementations, a combination of these operations can be performed such as extending the seed and storing the interval.

The use of an interval record in conjunction with one or more extend records thus enables a mapper and aligner to reduce the number of matching locations to be processed by the mapping and aligning unit through seed extension while also providing the mapping and aligning unit flexibility in determining whether matching reference locations identified using dynamic seed extension are accurate or, in some instances, whether seed extension using one or more extend records should even occur. This results in a mapping and aligning unit that uses less power and fewer computational resources while also being more accurate than other mapping and aligning units that avail themselves of the conventional seed extension techniques.

Generation of Hash Table Index for Flexible Seed Extension

FIG. 1 is a contextual diagram of a system 100 for generating a hash table index that facilitates flexible seed extension for hash table genomic mapping. The system 100 includes a computer 110, a memory 112, and a memory 130. Though the memories 112 and 130 are depicted in FIG. 1 as being separate memory devices, the present disclosure need not be so limited. Instead, in some implementations, the memory 112 and the memory 130 can be the same memory device. For example, the memory 112 and the memory 130 simply refer to two separate storage locations on a single memory device. Alternatively, the memory 112 and the memory 130 can each, respectively, be stored in separate memory devices such as separate hard disks accessible by the computer 110. By way of another example, the memory 112 can be a memory device of a cloud-based server storing a library of reference genomes and the memory 130 can be a local memory of the computer 110. Accordingly, the depiction of memory 112 and memory 130 as being separate memories in FIG. 1 places no limitation on the memories 112, 130 themselves, or the contents of those memories, and does not require that these memories must be organized or stored in any particular implementation of the present disclosure.

The computer 110 can include a computer, or multiple computers, that each includes one or more processing units that are configured to perform operations by executing one or more software instructions. The one or more processing units can include one or more central processing units (CPUs), one or more graphical processing units (GPUs), or any combination thereof. The computer 110 can be configured to interact with the memory 112, the memory 130, or the programmable circuit 162 directly via a direct connection such one or more busses, one or more USB cables, one or more USB-C cables, the like, or any combination thereof. Alternatively, or in addition, the computer 110 can be configured to interact with the memory 112, the memory 130, or the programmable circuit 162 via one or more networks. The one or more networks can include a wired Ethernet network, a wireless network, an optical network, a LAN, a WAN, a cellular network, the Internet, or any combination thereof.

By way of example, one implementation can include the computer 110 that is configured to (i) interact with the memory 112 and memory 130 stored in one or more local memory devices accessible to the computer 110 to generate a seed extension table 132 and hash table 140 and (ii) communicate, using one or more networks, the generated seed extension table 132 and hash table 140 to the programmable circuit 162 integrated with another device 160. The other device 160 can include a nucleic acid sequencer, a cloud-based server(s), or any other computer. In some implementations, the programmable circuit 162 can be integrated with the other device using an extension card such as a PCI card. In such implementations, the programmable circuit 162 can be housed on a logic board of a PCI card that is inserted into a motherboard of the sequencer, cloud-based server, or other computer, using a PCI port on the motherboard.

The programmable circuit 162 can include one or more programmable integrated circuits such as one or more Field Programmable Gate Arrays (FPGAs). Field programmable gate arrays are integrated circuits that include multiple hardware digital logic gates, hardware digital logic circuits, or the like, that are dynamically configurable to implement one or more processing modules such as genomic analysis modules of a genomic analysis pipeline such as a mapping and aligning unit 170, or a portion of a processing module such as the hash table 140. FPGAs can be programmed using a hardware description language (HDL) such as Very High Speed Integrated Circuit Hardware Description Language (VHDL), Verilog, or the like. FPGAs are flexible, in that an FPGA that has been previously programmed to include one or more genomic analysis modules of a genomic analysis pipeline, or portions thereof, can be dynamically reconfigured to include updates to the one or more genomic analysis modules, other different genomic analysis modules, or the like.

Other types of integrated circuits can be used instead of, or in addition to, the programmable circuit 162 to realize the functionality of the programmable circuit 162 described herein. For example, one or more Application Specific Integrated Circuits (ASICs) can be used to realize the functionality, or a portion of the functionality, of the programmable circuit 162. ASICs are custom integrated circuits that include multiple hardware digital logic gates, multiple digital logic circuits, or the like, that are configured at the time of manufacture. ASICs are similar to the FPGAs described herein in that the hardware digital logic gates or multiple digital logic circuits of the ASIC can be described or designed using a hardware description language such VHDL, Verilog, or the like. Then ASICs can be manufactured, or printed, to include the digital logic or digital circuitry described by the HDL. Once manufactured or printed, however, an ASIC cannot be dynamically reconfigured like an FPGA. Though the examples described herein describe programmable or custom circuits, the present disclosure need not be so limited. In some implementations, for example, other types of integrated circuits can be used to realize the functionality described as being performed by the programmable circuit 162.

The memory 112 can store one or more reference sequences 114. A reference sequence can include (i) an entire reference genome that is representative of a species, (ii) a portion of a reference genome that is representative of a species, or (iii) full and/or partial reference genomes that are representative of multiple species. The reference sequence includes a sequential listing of bases or nucleotides. The sequential listing of bases or nucleotides, of which the reference sequence is comprised, can be organized in the memory 112 as a digital nucleic acid sequence database. A particular reference sequence can be assembled, by persons, computers, or both, from multiple different donors of a particular species, as a representative of the species.

In some implementations, the particular reference sequence can be assembled as representative of a particular population, where the particular population is subset of the species having certain nucleic acid sequences that may uniquely set apart the particular population from other populations within the species. A species can include any species including humans, non-human mammals, reptiles, fish, insects, plants, bacteria, viruses, or the like. A reference sequence can be generated from samples of non-extinct species such as humans or from currently extinct species such as a population of dinosaurs or mammoths. Reference sequences for extinct species such as a dinosaur may be assembled using samples obtained from biological material contained within fossilized, frozen, or otherwise preserved remains of the extinct species. Reference sequences for extinct species may be assembled from a combination of (i) sequencing of biological remains obtained from fossilized remains of the extinct species and (ii) sequencing of biological samples from non-extinct species. An entire reference genome can include many sequential bases or nucleotides. For example, a human reference genome can include as many as 3 billion sequential bases or nucleotides.

The computer 110 is configured to generate a hash table 140 that facilitates flexible seed extension. The computer 110 begins generating a hash table 140 by accessing the reference sequence 114 stored in the memory 112 and obtaining a seed 114-1, 114-2, 114-3, to **114-*n* of the reference sequence, wherein n is any non-zero integer greater than zero. In some implementations, the computer 110 can identify and obtain a seed 114-1, 114-2, 114-3, to 114-*n* of the reference sequence 114 using a seed access window. The computer 110 can initialize the seed access window to be of a seed length K, where K is the number of bases or nucleotides to be included in each seed, wherein K is any non-zero integer greater than zero. The computer 110 can begin accessing seeds of the reference sequence 114 by positioning the seed access window of length K at the beginning of a reference sequence to encompass a first set of K nucleotides in the reference sequence such as seed "GTTTA" 114-1. In this example, K is equal to 5, but K is not limited to such a nucleotide length. Instead, K can be equal to any non-zero integer greater than zero, and in some implementations may be equal to, for example, 7, 10, 12, 15, 18, 20, 21, 25, or more bases or nucleotides. The seeds 114-1, 114-2, and 114-3 to 114-***n* are merely examples of seeds of a reference sequence 114 and need not correspond, in this example, to a set of 4 sequence seeds of the reference sequence 114.

To generate the hash table 140, the computer 110 is configured to access each seed 114-1, 114-2, and 114-3 to 114-*n* of the reference sequence 114 and perform a set of operations for each seed 114-1, 114-2, and 114-3 to 114-*n*. The set of operations are designed to generate information for storage into hash locations 144 of the hash table 140 corresponding to the index keys 142 of the hash table 140. Each index key 142 can correspond to a respective seed of the multiple seeds 114-1, 114-2, 114-3 to 114-*n* of the reference sequence 114, a reverse complement of each of the seeds 114-1, 114-2, 114-3 to 114-*n*, an extended seed of one or more of the multiple seeds 114-1, 114-2, 114-3 to 114-*n*, or a reverse complement of each of the extended seeds. Each of the index seeds 142 can be mapped to a hash location 144 using the hash function 143.

The computer 110 can identify and access each seed of the multiple seeds 114-1, 114-2, and 114-3 to 114-*n* by advancing the seed access window K locations in the reference sequence 114 after each respective seed is accessed and used to perform the set of operations. The set of operations performed on each respective seed 114-1, 114-2, and 114-3 to 114-*n* is described in more detail below. The set of operations can include population of the hash table 140 using the generated information. Alternatively, population of the hash table 140 can occur after the set of operations is concluded for each seed.

The set of operations the computer 110 performs, on each seed 114-1, 114-2, and 114-3 to 114-*n* of the reference sequence 114, begins with the computer 110 obtaining the seed identified by the seed access window. In the example of FIG. 1, assume that a seed of the reference sequence 114 identified by the seed access window is "GTTTA" 114-1.

The computer 110 can determine whether the obtained seed "GTTTA" 114-1 matches more than a predetermined number of reference sequence 114 locations. A matching reference sequence location can include a subset of the reference sequence 114 that includes the seed 114-1. The subset of the reference sequence 114 can include set of sequentially ordered nucleotides that is greater than, or equal to, the K-number of nucleotides in the obtained seed. In some implementations, a predetermined number of matching reference sequence locations can include one matching reference sequence location. However, in other implementations, the predetermined number can be set to more than one matching reference sequence location.

If the computer 110 determines that the seed 114-1 matches fewer than, or equal to, a predetermined number of reference sequence locations, then the computer can populate the reference location(s) that match the seed 114-1 into a hash location 144 reached by the seed "GTTTA" 114-1. A hash location 144 can be "reached by" a seed such as seed 114-1 if the seed 114-1 matches a hash key 142 that the hash function 143 maps to the hash location. Alternatively, if the computer 110 determines that the predetermined number of matching reference sequence locations is more than the predetermined number of reference sequence locations, then the computer 110 can generate a seed extension tree for the seed 114-1. In the example of FIG. 1, the computer 110 determines that the seed "GTTTA" 114-1 matches more than a predetermined number of reference sequence locations. Accordingly, the computer 110 generates a seed extension tree 120 for the seed 114-1.

The computer 110 can generate the seed extension tree 120 for the seed 114-1 on a node-by-node basis beginning with the root node 120. The seed extension tree 120 can be generated such that a set of matching reference locations identified by a leaf node does not exceed a predetermined match limit unless no further seed extension is possible. Each node of the seed extension tree 120 can include a seed and an interval of contiguous addresses in a seed extension table 132. In some implementations, the seed extension table 132 includes a center-lexicographically sorted list of 131-1 to 131-6 reference sequence locations that match a seed such as seed 114-1 obtained by the computer 110 using the seed access window. Center-lexicographically sorting can include, for example, establishing a priority order of symbol positions, and then alternating left and right outward from the center symbol. Alternatively, center-lexicographically sorting can include, for example, establishing a priority order of symbol positions, and then alternating right and left outward from the center symbol. Yet, even other variations can be used.

In the example of FIG. 1, the seed extension table 132 is center-lexicographically sorted 133 based on the seed 114-1 of "GTTTA". This example assumes a left-first order and a normal alphabetical nucleotide order (i.e., A, C, G, T) to achieve the center-lexicographical sort order shown in FIG. 1. The computer 110 can generate a seed extension table such as the seed extension table 132 for each seed 114-1, 114-2, 114-3, 114-*n* determined to have more than a predetermined threshold number of matching reference sequence locations. In some implementations, the seed extension table 132, for each qualifying seed, may be generated for a particular seed after the computer 110 access the particular seed using the seed access window and before the seed extension tree 120 for the seed is generated.

The description of the nodes of the seed extension tree 120 above indicates the interval of addresses of each node is contiguous. However, the present disclosure need not be so limited. Instead, the interval of addresses of a node may be non-contiguous. For example, certain implementations may use an interval to describe of a plurality of different sets of one or more contiguous locations of a seed extension table, or other data structure stored in one or more memory devices, where each contiguous set of one or more contiguous locations is non-contiguous with respect to each other. That is, there can exists a break in continuity between each respective set.

The seed extension table for each qualifying seed can be stored in the memory 130. This can result in n seed extension tables—i.e., one for each of the n seeds of the reference sequence 114. Alternatively, the number of seed extension tables may be less than n, such as if seed extension tables are only generated and stored for seeds having more than a predetermined threshold number of matching reference sequence locations. After generation of each of the seed extension tables, a set 132A of each of the seed extension tables can be provided to the device 160 housing the programmable circuit 162 and be stored in the memory 180 that is accessible to the programmable circuit 162. The memory 180 can include a DRAM memory, SRAM memory, NAND memory, or the like. In some implementations, the set 132A of seed extension tables can be provided to the device 160 housing the programmable circuit 162 as individual seed extension tables. In other implementations, the set 132A of seed extensions tables may be provided as a single, master seed extension table that is comprised of a concatenation of each of the respective seed extension tables for each seed. The set 132A of seed extension tables can be provided in any number of formats. In some implementations, the set 132A of seed extension tables can be compressed by the computer 110 to reduce the size of the seed extension table file provided to the device 160 and then decompressed by the device 160, programmable circuit 162, or the like for storage in the memory 180.

The computer 110 can generate the root node 121 of the seed extension tree 120 to include the seed "GTTTA" 121*a* and the interval A 121*b*. The interval A 121*b* identifies a contiguous interval of locations in the seed extension table 132 that stores reference sequence locations matching the seed "GTTTA" 121*a* represented by the root node 121. In this example, the interval A identifies the location of the seed extension table 132 that spans 131-1 to 132-6 and includes "TAGTTTACT," "TAGTTTATC," "GAGTTTATG," "ACGTTTAGT," "TCGTTTAGT," and "ACGTTTAGC." The computer 110 can determine the appropriate interval, or intervals, for a particular seed of a node such as node 121 by accessing the seed extension table 132 to determine the locations of the seed extension table 132 having reference sequence locations that match the seed of the node 121.

In some implementations, the interval 121*b* for a particular seed of a node such as node 121 can be described using a start location address of the interval in the seed extension table 132 and an end location address of the interval in the seed extension table 132. In other implementations, the interval 121*b* for a particular seed of a node such as node 121 can be described using a start location address of the interval in the seed extension table 132 and an offset from the start location address. In such implementations, the interval can later be calculated using the start and end addresses of the interval or the start address of the interval and the offset. However, the present disclosure need not be so limited. Instead, it is understood that an interval record may be represented in the hash table location 144 using any form of information that is structured or unstructured in any appropriate manner. For example, in some implementations, an interval record can be implemented using one record of a fixed size and format. In other implementations, an interval record can be implemented by selecting among multiple formats of different sizes, comprising record counts or the like to optimize the storage space consumed by the hash table 140, enable compressibility of the hash table 140, improve efficiency of hash queries relative to other interval record formats, or the like.

The computer 110 can continue generation of the seed extension tree 120 by extending the number of bases or nucleotides for the seed 121*a* identified in the root node. For example, the computer 110 can extend the seed length of the root node from 5 bases or nucleotides to 7 bases or nucleotides and identify the largest subset of reference sequence locations in the seed extension table having 7 matching bases or nucleotides. In the example of FIG. 1, the computer 110 can determine that the largest subset of reference sequence locations having 7 matching nucleotides is "CGTTTAG." The interval B identifies a contiguous interval of locations in the seed extension table 132 that stores reference sequence locations matching the seed "CGTTTAG." In this example, the interval B identifies the location of the seed extension table 132 that spans 132-4 to 132-6 and includes "ACGTTTAGT," "TCGTTTAGT," and "ACGTTTAGC." The computer 110 can generate node 122 using the information determined using the seed extension table 132. For example, the computer 110 can generate node 122 to include a seed "CGTTTAG" 122*a* and an interval B 122*b*.

With reference to the example of FIG. 1, the computer 110 can continue generation of the seed extension tree 120 by determining whether there are other reference sequence locations in the seed extension table having 7 matching bases or nucleotides. If there are other reference sequence locations in the seed extension table 132 having 7 matching bases or nucleotides, the computer 110 uses the next largest set of reference sequence locations having 7 matching bases or nucleotides to generate the next node of the seed extension tree. In the example of FIG. 1, the computer 110 can determine that the next largest subset of reference sequence locations have 7 matching nucleotides is "AGTTTAT." The interval E identifies the contiguous interval of locations in the seed extension table 132 that store reference sequence locations matching the seed "AGTTTAT." In this example, the interval E identifies the location of the seed extension table 132 that spans 132-2 to 132-3 and includes "TAGTTTATC" and "GAGTTTATG." The computer 110 can generate node 123 using the information determined using the seed extension table 132. For example, the computer 110 can generate node 123 to include a seed "AGTTTAT" 123*a* and an interval E 123*b*.

With reference to the example of FIG. 1, the computer 110 can continue generation of the seed extension tree 120 by determining whether there are other reference sequence locations in the seed extension table having 7 matching bases or nucleotides. If other reference sequence locations in the seed extension table are identified as having 7 matching bases or nucleotides, then the computer 110 can generate a new node of seed extension table 120 using the next largest set of reference sequence locations having 7 matching bases or nucleotides, as described above. However, in this example of FIG. 1, there are no other reference sequence locations in the seed extension table 132 having 7 matching bases or nucleotides. Accordingly, the computer 110 can determine to extend the number of bases of nucleotides from 7 to 9 and continue analyzing the reference sequence locations in the seed extension table 132.

With reference to the example of FIG. 1, the computer 110 can identify the largest subset of reference sequence locations having 9 matching nucleotides. In this example, there are multiple subsets of reference sequence locations having 9 matching nucleotides. In such instances, the computer 110 can determine to create a node of a seed extension tree for each set of reference sequence locations having 9 matching reference sequence nucleotides. In some implementations, the computer 110 may determine the order of creation of seed extension tree nodes randomly. In other implementations, the computer 110 can begin to generate the subsequent extension tree nodes based on their center lexicographic order.

Regardless of their order of creation, the computer 110 can continue by generating nodes of the seed extension table for each subset of reference sequence locations having 9 matching nucleotides. By way of example, the computer 110 can generate the node 124 of the seed extension tree 120 to include the extended short seed "TCGTTTAGT" 124*a* and the interval C 124*b*. The interval C 124*b* identifies the contiguous interval of locations in the seed extension table 132 that stores reference sequence locations matching the short seed "TCGTTTAGT" 124*a*. In this example, the interval C identifies the location of the seed extension table 132 that spans 132-5 and includes "TCGTTTAGT." The computer 110 can determine the appropriate interval for a particular short seed of a node such as node 124 by accessing the seed extension table 132 to determine the locations of the seed extension table 132 having reference sequence locations that match the short seed of the node 124.

With reference to the example of FIG. 1, the computer 110 can continue by generating nodes of the seed extension table for each subset of reference sequence locations having 9 matching nucleotides. By way of example, the computer 110 can generate the node 125 of the seed extension tree 120 to include the extended short seed "ACGTTTAGC" 125*a* and the interval D 125*b*. The interval D 125*b* identifies the contiguous interval of locations in the seed extension table 132 that store reference sequence locations matching the short seed "ACGTTTAGC" 125*a*. In this example, the interval D identifies the location of the seed extension table 132 that spans 132-6 and includes "ACGTTTAGC." The computer 110 can determine the appropriate interval for a particular short seed of a node such as node 125 by accessing the seed extension table 132 to determine the locations of the seed extension table 132 having reference sequence locations that match the short seed of the node 125.

With reference to example of FIG. 1, the computer 110 can continue by generating nodes of the seed extension table for each subset of reference sequence locations having 9 matching nucleotides. By way of example, the computer 110 can generate the node 126 of the seed extension tree 120 to include the extended short seed "TAGTTTATC" 126*a* and the interval F 126*b*. The interval F 126*b* identifies the contiguous interval of locations in the seed extension table 132 that store reference sequence locations matching the short seed "TAGTTTATC" 126*a*. In this example, the interval F identifies the location of the seed extension table 132 that spans 132-2 and includes "TAGTTTATC." The computer 110 can determine the appropriate interval for a particular short seed of a node such as node 126 by accessing the seed extension table 132 to determine the locations of the seed extension table 132 having reference sequence locations that match the short seed of the node 126.

The present disclosure describes an example of constructing a seed extension table in a particular, methodical order that proceeds from a largest set of matching bases to a smallest set of matching bases. However, the present disclosure need not be limited to use of seed extension trees that are constructed in this manner. Instead, any process for constructing a seed extension table can be used, so long as the result of the seed extension table construction process yields a seed extension table. For example, a seed extension tree can be generated from a smallest set of matching bases to a largest set of matching bases, or in no particular order at all. In some implementations, a previously generated seed extension table can be generated and used by the system 100 without the requirement that the seed extension table be constructed by the system 100.

The computer 110 can populate hash locations 144 of the hash table 140, which are reached by particular seed inputs that correspond to particular hash index keys 142, using the generated seed extension tree 120. By way of example, the computer 110 can determine whether the node 121 is a leaf node. Based on a determination that the node 121 is not a leaf node, the computer 110 can populate a hash location 144-*y* using the root node 121, where y is any non-zero integer. Populating the hash location 144-*y* using the root node 121 can include storing an interval record 153*b* into the hash table location 144-*y* that is reached by the seed 121*a*. The interval record 153*b* identifies the interval 121*b* for the node 121. The hash table 140 can include a hash table index key 142 for each seed 114-1, 114-2, 114-3 to 114-*n*, a reverse-complement of each seed 114-1, 114-2, 114-3 to 114-*n*, or a combination thereof. Each hash table index key 142 can be mapped to one or more hash locations 144 using the hash function 143. Each hash location 144 can be implemented using one or more storage buckets, where a storage bucket corresponds to a set of one or more storage locations of a memory device. Each of the one or more storage locations of the memory device may be contiguous or non-contiguous memory locations.

The example of FIG. 1 shows only a portion of the hash table 140 having keys 142 that corresponds to a forward seed of seeds 121, 122, 123, and 125. However, the present disclosure need not be so limited. For example, in some implementations, seeds can be hashed using the hash function 143 in such a manner that a reverse-complement nucleotide sequence of any seed results in the same hash as the original forward seed. A reverse-complement of a nucleotide sequence can be determined by reversing the order of the original nucleotide sequence and swapping As with Ts, Ts with A, Cs with Gs, and Gs with Cs. By way of example, a hash key 142 for the original forward seed GTTTA 121*a* can have the same hash as the hash key 142 for the reverse complement of the seed GTTTA, which is TAAAC. In such implementations, when matching reference sequence locations are stored in a hash location 144 or as entries in the seed extension table 132, their sequence orientation can be annotated using, for example, a reverse-complement (RC) flag. However, in other implementations, a reverse-complement of a seed may result in a different hash, and no orientation need be annotated in matching reference sequence locations stored in hash location 144 of the hash table 140 or the seed extension table 132.

Populating a location 144 of the hash table 140 can also include determining whether an extend record is to be populated into the hash location 144. Determining whether an extend record should be populated into the hash location 144 can include determining whether a node of the seed extension tree 120 that is being used to populate the hash location is a leaf node. If the node is determined to be a leaf node, then the computer 110 can determine to not store an extend record in the hash location that is reached by the seed associated with the node. Alternatively, if the node is determined to not be a leaf node, then the computer 110 can generate an extend record and store the generated extend record in a hash table location 144. With reference to the example of FIG. 1, the computer 110 can determine, or have previously determined, that the node 121 is not a leaf node. In such instances, the computer 110 can generate and store an extend record 153*a* in the hash table location 144-*y* that is reached by the seed 121*a*. Accordingly, the hash location 144-*y* can include an extend record 153*a* and an interval record 153*b*.

An extend record can include one or more instructions that, when executed by a computer such as a central processing unit (CPU) or graphics processing unit (GPU) executing software instructions or programmable circuit 162, can cause the CPU, GPU, or programmable circuit 162 to extend the seed used in the hash query that reached the hash location storing the extend record by one or more nucleotides. In some implementations, an extend record can be generated such that the extend record instructs a computer to extend a seed symmetrically on each end of the seed. Accordingly, by way of example, an extend record can be generated to instruct a computer such as a CPU, GPU, or the programmable circuit 162 to extend a seed by two nucleotides, four nucleotides, six nucleotides, or the like. In such implementations, symmetrical extension of the seed can be achieved by extending the seed by one nucleotide on each respective end of the seed, two nucleotides on each respective end of the seed, three nucleotides on each respective end of the seed, or the like. In the example of FIG. 1, the extend record 153*a* is configured to extend an initial seed 121*a* by 2-bases symmetrically. The computer 110 can determine an extension length for inclusion in an extend record based on a variety of factors that include (i) a number reference sequence locations that match the seed, (ii) a number of runtime seed extension iterations that are desired, (iii) a number of matching reference sequence locations sought for each iteration, or the like. Runtime flexible seed extension using the hash table 140 is described in more detail below with respect to FIG. 3.

Seeds of nucleotides have generally been described as being comprised of contiguous sets of sequential nucleotides. Similarly, the extend records are described as sequentially extending the contiguous set of sequential nucleotides by one or more additional nucleotides in manners which may be symmetric or asymmetric, yet still contiguous. However, the present disclosure is not limited to the use of contiguous sets of sequential nucleotides. Instead, seeds of a read or a reference sequence can be noncontiguous patterns of seeds from a read or the reference sequence. Similarly, an extend record can include instructions that, when processed by a CPU, GPU, or programmable circuit 162, cause the CPU, GPU, or programmable circuit 162 to extend an initial seed to incorporate noncontiguous nearby bases or nucleotides. In such implementations, matching reference sequence locations for each root node seed may be sorted in seed extension table 132 lexicographically in a manner that accounts for use of noncontiguous seeds.

The computer 110 can continue populating information into the hash locations 144 for each remaining node 122, 123, 124, 125, 126 of the seed extension tree 120. By way of example, the computer 110 can determine whether the node 122 is a leaf node. Based on a determination that the node 122 is not a leaf node, the computer 110 can populate a hash location 144-3 using the node 122. Populating the hash location 144-3 using the node 122 can include storing an interval record 152*b* into the hash table location 144-3 that is reached by the seed 122*a*. The interval record 152*b* identifies the interval 122*b* for the node 122. The computer 110 can determine, or have previously determined, that the node 122 is not a leaf node and generate an extend record 152*a* for storage in the hash location 144-3. In the example of FIG. 1, the extend record 152*a* includes instructions to extend the seed 122*a* by 2 bases or nucleotides symmetrically. These instructions of the extend record 152*a* can be executed, at run time, if, for example, the interval B is not accessed in response to a query for the seed 122*a*.

However, the presented disclosure is not so limited as other extend record scan also be generated that instruct a CPU, GPU, or the programmable circuit 162 to extend a seed by different additional nucleotide lengths (e.g., 2, 4, 6, 8, etc.) or in different manners (e.g., non-symmetrically using additional nucleotide lengths of 1, 3, 5, etc.). Though the example of FIG. 1 shows a single extend record in the hash location 144-3, the present disclosure is not so limited. Instead, in some implementations, multiple extend records can be stored at a single hash location 144-3. For example, the computer 110 can also store one or more additional extend records in the hash location 144-3 that are configured to extend the initial seed 122*a* by four bases. In such implementations, a CPU, GPU, or programmable circuit 162, at run time, can first attempt to extend the initial seed 122*a* by four bases. If such seed extension fails, because a subsequent query of the hash table 140 at runtime yields no matching reference sequence locations, then the CPU, GPU, or programmable circuit can obtain the other extend record 152*a* that includes instructions to extend the initial base by only 2 bases. This can increase the likelihood that matching reference sequence locations are returned.

The computer 110 can continue populating information into the hash locations 144 for each node 123, 124, 125, 126 of the seed extension tree 120. By way of example, the computer can determine whether the node 123 is a leaf node. Based on a determination that the node 123 is not a leaf node, the computer 110 can populate a hash location 144-1 using the node 123. Populating the hash location 144-1 can include storing an interval record 150*b* into the hash table location 144-1 that is reached by the seed 123*a*. The interval record 150*b* identifies the interval 123*b* for the node 123. The computer 110 can determine, or have previously determined, that the node 123 is not a leaf node and generate an extend record 150*a* for storage in the hash location 144-1. In this example, the extend record 150*a* includes instructions to extend the seed 123*a* by 2 bases or nucleotides symmetrically. These instructions of the extend record 150*a* can be executed, at run time, if, for example, the interval E is not accessed in response to a query for the seed 123*a*.

The computer 110 can continue populating information into the hash locations 144 for each node 124, 125, 126 of the seed extension tree 120. By way of example, the computer 110 can determine whether the node 125 is a leaf node. Based on determination that the node 125 is a leaf node, the computer 110 can determine to populate the hash table 140 by storing the matching reference sequence locations 155 identified by the interval D 125*b* that match the seed "ACGTTTAGC" into the hash location 144-2. Alternatively, in other implementations, the computer 110 can determine to store an interval record into hash location 144-2 that identifies the interval D 125*b*. Such a determination may be made by the computer 110, in some implementations, based on whether storage of each of the matching reference sequence locations in hash table locations 144 for leaf nodes is an optimal use of memory resources. Accordingly, if it is determined that storage of matching reference sequence locations in hash table locations 144 for leaf nodes does not satisfy a predetermined threshold usage of memory resources, then the computer 110 can store matching reference sequence locations into hash locations that are reached by seeds of a leaf node of a seed extension tree. Otherwise, if this memory resource usage threshold is exceed, the computer 110 can store an interval record in hash locations 144 reached by seeds of a leaf node of a seed extension tree. The computer 110 can determine, or have previously determined, that the node 125 is a leaf node, and not generate an extend record for storage in the hash location 144-2. Accordingly, no further extensions of the seed "ACGTTTAGC" would occur at run time in this example.

As described above, the hash location 144-2 can store only the matching reference sequence locations that match the seed 125*a* and correspond to hash key 142-1. This is because, in this example, the seed 125*a* is a leaf node 125 seed that cannot be extended. However, a population of reference sequence locations without one, or both, of an extend record or an interval record is not limited to hash locations 144 that are reached by seeds of leaf nodes. Instead, the computer 110 can determine to populate a hash location 144 with matching reference sequence locations without one, or both, of an extend record or an interval record in other instances. For example, in some implementations, if the computer 110 determines that the seed extension table 132 for a particular seed only identifies an interval of matching reference sequence locations that is less than a threshold number of matching reference sequence locations, then the computer 110 can populate a hash location 144 that is reached by the particular seed with the matching reference sequence locations without one, or both, of an extend record or an interval record.

Other types of information can be stored in a hash location 144 of the hash table 140. For example, the computer 110 can receive an instruction to insert one or more "STOP" records into a hash location 144 of the hash table 140. Such "STOP" hash records can cause a particular hash location 140 storing an interval record or a set of one or more matching reference locations to return either (i) the interval record or (ii) the set of one or more matching reference locations without further extension of the seed that was used to reach the hash location. In other implementations, the computer 110 can receive an instruction to insert a "STOP" record into a hash location that already includes an extend record. In such implementations, when a CPU, GPU, or programmable circuit 162 encounters a "STOP" record, the CPU, GPU, or programmable circuit 162 can conditionally determine whether to (i) disregard the extend record and return (i) an interval record or (ii) a set of one or more matching reference locations that match the seed used to reach the hash location having the "STOP" record or (ii) execute the seed extension described by the extend record. In some implementations, the conditional determination can be made based on one or more factors such as a number of matching reference sequences identified by (i) the interval record or (ii) the set of one or more matching reference sequence locations. Accordingly, insertions to insert one or more "STOP" records into particular hash locations responsive to respective input seeds can be used as a design tool to avoid a fixed maximum mismatches problem without rebuilding a hash table such as hash table 140.

The computer 110 can continue to populate information iteratively into the hash locations 144 for each remaining node the seed extension tree 120 such as nodes 124, 126. Entries for each of these leaf nodes can be populated in the manner described above with respect to node 125, as nodes 124, 126 are leaf nodes like node 125.

In addition, the computer 110 can continue to apply the processes described above iteratively in the example of FIG. 1 with reference to the seed "GTTTA" 114-1 to each seed of the reference sequence 114. For example, once seed "GTTTA" 114-1 has been processed as described above, the computer 110 can advance the seed access window to the next subsequent seed in the reference sequence, access the seed, and then iteratively perform the processes described above with reference to seed "GTTTA" 114-1 to each of the n seeds of the reference sequence. These processes can include obtaining the seed identified by the seed access window, determining whether the seed has more than a predetermined number of matching reference sequence locations, generating a seed extension tree if there exists more than a predetermined number of matching reference sequence locations, and then populating the hash table 144 using the seed and interval identified by the nodes of the seed extension tree. In some implementations, the computer 110 can also iteratively perform the same processes described above with reference to seed "GTTTA" 114-1 to the reverse complement for each of the n seeds of reference sequence 114. The culmination of these iterative processes for each reference seed and each reverse complement can result in a hash table 140 that has x index entries and y hash locations where x and y are each in the hundreds of millions, or even billions for a particular reference sequence such as a human genome.

Figure 2:
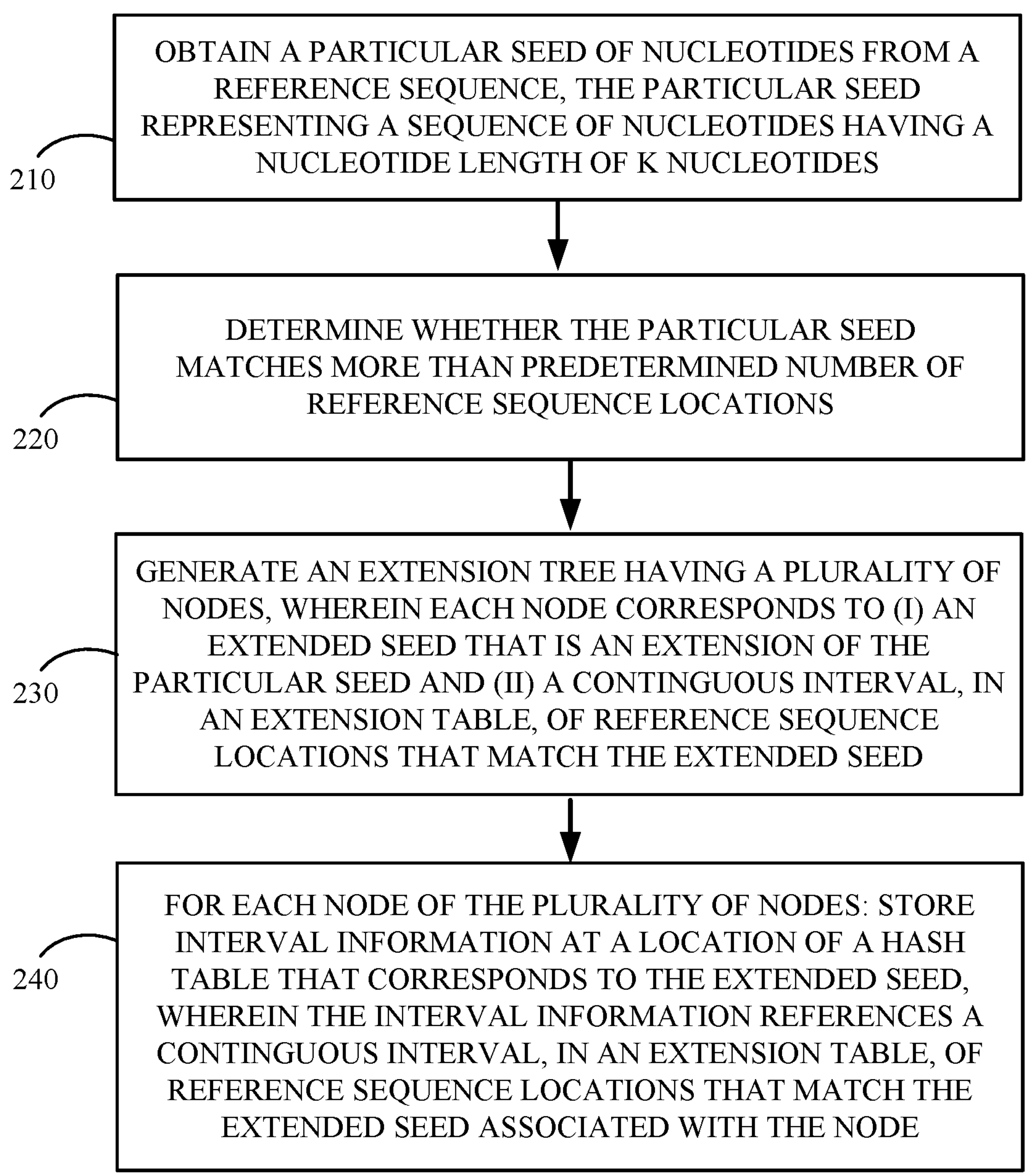
FIG. 2 is a flowchart of a process for generating a hash table index that facilitates flexible seed extension for hash table genomic mapping.
Figure 3:
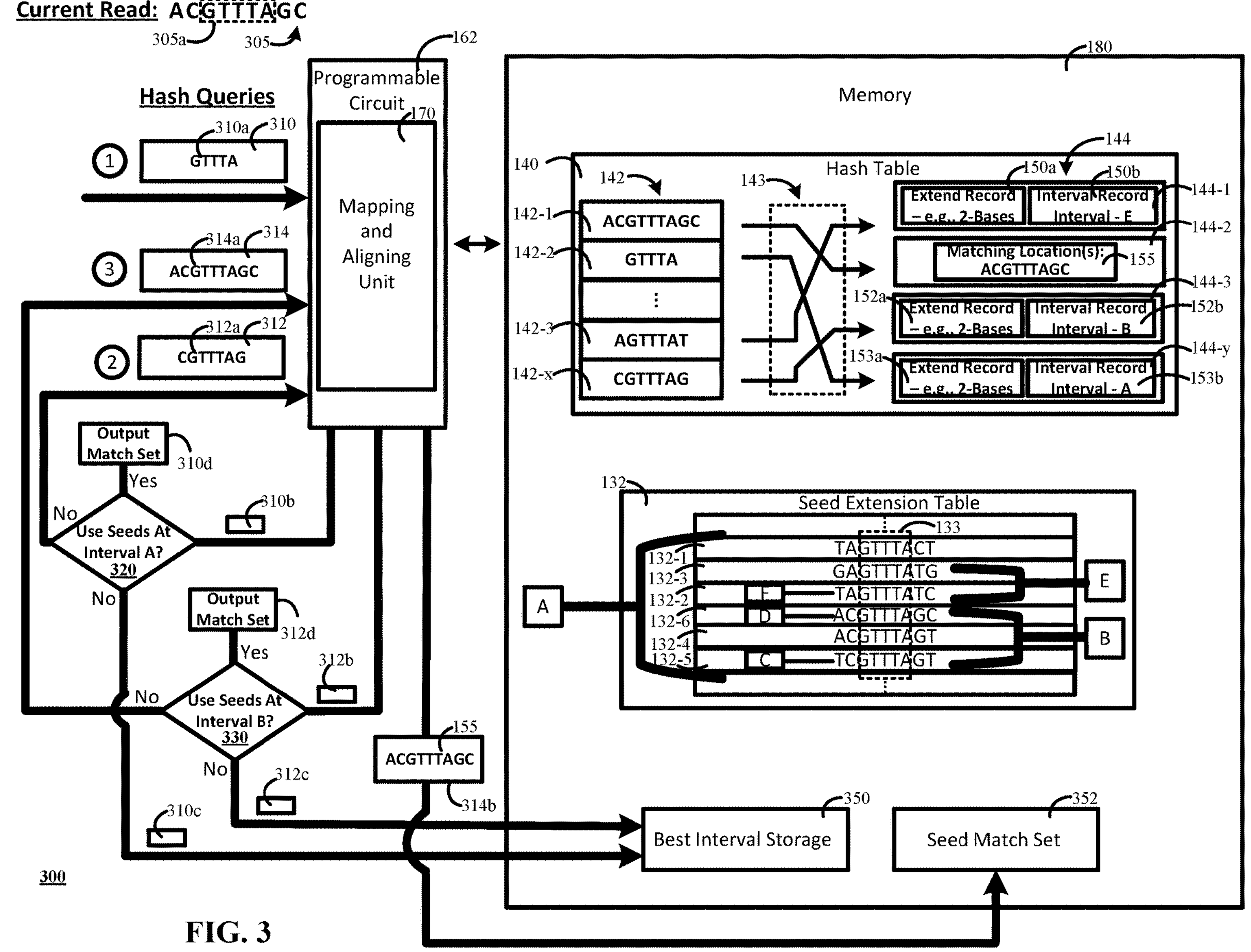
FIG. 3 is a contextual diagram of a run-time system for performing run-time flexible seed extension for hash table genomic mapping.
Figure 4:
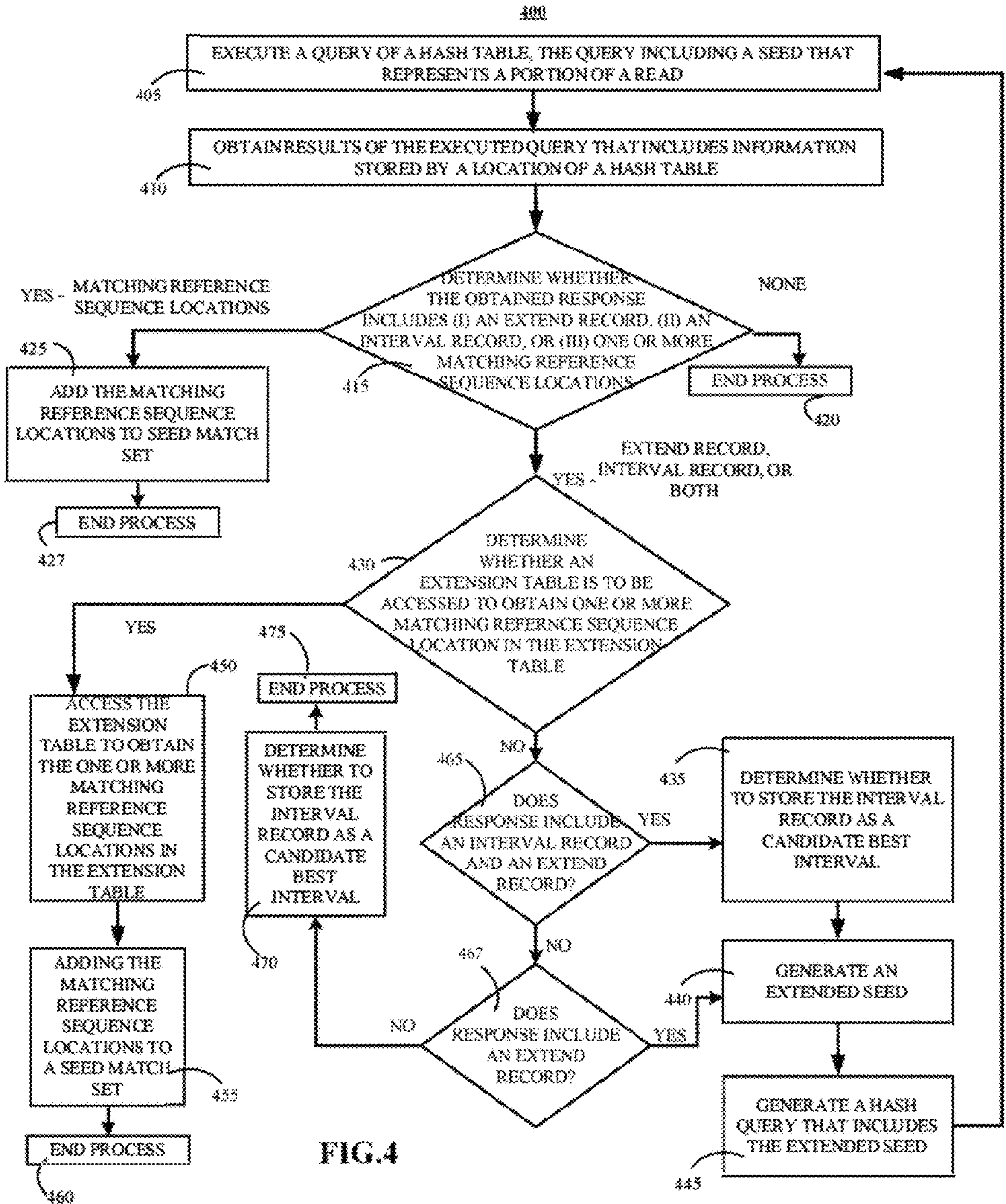
FIG. 4 is a flowchart of a process for performing runtime flexible seed extension for hash table genomic mapping.

In some implementations, the hash table 140 can be used by a computer such as the computer 110 to perform runtime flexible seed extension by executing hash queries against the hash table 140 in software using one or more CPUs, GPUs, or a combination thereof to execute software instructions that, when executed, cause the one or more CPUs, GPUs, or combination thereof to perform the processes described with respect to FIGS. 3 and 4. In other implementations, the computer 110 can generate a hash table installation package that includes software instructions for installing the hash table 140 and a set 132A of seed extension tables on another computer. For example, the hash table installation package can include software instructions that, when executed, perform the operations described by the process 200 of FIG. 2. The computer 110 can provide the hash table installation package that includes the software instructions to the other computer. The other computer can receive the hash table installation package and install the hash table 140 and set 132A of seed extension tables. The other computer can then perform runtime flexible seed extensions by executing hash queries against the hash table 140 in software using one or more CPUs, GPUs, or a combination thereof, to execute software instructions that, when executed, cause the CPUs, GPUs, or a combination thereof to perform the processes described with respect to FIGS. 3 and 4.

However, in some implementations, the computer 110 can generate a hash table installation package 146 that includes hardware programming language instructions that can configure the programmable circuit 162 to implement the mapping and aligning unit 170 in hardware digital logic circuits. The hardware programming language instructions can be in the form of a file such as a binary bitstream file. The binary bitstream file can be generated, prior to its inclusion in the hash table installation package 146, by compiling hardware programming language code such as VHDL, Verilog, or the like that describes the circuitry to be implemented by the programmable circuit 162. The hardware programming language instructions of the hash table installation package, when processed by the programmable circuit 162, can cause the programmable logic circuit to program dynamically configurable logic circuits of the programmable logic circuit to implement the flexible seed extension by executing hash queries against the hash table 140 in hardware using the processes described with respect to FIGS. 3 and 4. The hash table installation package 146 can also include the set 132A of seed extension tables and instructions for installing the set 132A of seed extension tables in a memory 180 accessible to the programmable circuit 162. The hash table installation package 146 can also include the hash table 140 and instructions for installing the hash table 140 in the memory 180 accessible to the programmable circuit 162. The programmable circuit 160 can be programmed to use the hash table 140 as part of the mapping/aligning unit 170 to perform mapping of short seeds to a reference sequence as discussed in more detail herein with respect to FIG. 3. The computer 110 can provide the hash table installation package to the device 160 such as a desktop computer, a laptop computer, a tablet computer, a smartphone, a cloud-based server, a sequencer, or other device that houses the programmable circuit 160 using one or more networks, a direct connection such as one or more busses, a USB cable, a USB-C cable, or any combination thereof. The device 160 can receive the hash table installation package and program the programmable circuit 162 to implement the mapping and aligning unit 170 in hardware logic gates of the programmable circuit 162 using the hardware programming language instructions of the hash table installation package.

Accordingly, the respective hash table installation packages 146 can be used to manage installation, use, and even removal of the hash table 140 and seed extension table in a variety of different manners. For example, in some implementations, the hash table 140 and sets 132A of seed extension tables can each be stored as a file on hard disk or other storage medium and then each can be loaded into a common memory prior to runtime access, such as DRAM that comprises one or more components or modules to implement runtime flexible seed extension, as described with respect to the processes described herein in reference to FIGS. 3 and 4. However, in other implementations, the hash table 140 or sets 132A of seed extension tables may be stored together or separately, each as one or more distinct contiguous portions in a memory device or non-contiguous portions of a memory device. Likewise, the hash table 140 or sets 132A of seed extension tables can be compressed or uncompressed, stored on common or separate storage media and/or memory, or cached or uncached, during runtime mapping or otherwise so long as there is some pathway and method for the runtime mapping and aligning unit 170 to access selected portions of both the hash table 140 and the sets 132A of seed extension tables. In yet other implementations, the hash table 140 can be implemented entirely in hardware logic circuits of a programmable circuit 162 and the sets 132A of seed extension tables can be stored in a memory 180 accessible by the programmable logic circuit 162 such as a DRAM memory unit. In yet other implementations, the hash table 140 can be stored in a memory 180 that is accessible by the programmable logic circuit 162 such as a DRAM memory unit and the sets 132A of seed extension tables can be implemented entirely in hardware logic circuits of a programmable circuit 162.

In some implementations, the computer 110 can also generate an installation package that includes a hash table and seed extension builder as described herein. The computer 110 can provide the installation package to another computer over the network. The installation package can be used to install the hash table and seed extension builder on the other computer, or a different computer, to enable the party that receives and installs the hash table and seed extension builder to build their own hash table and seed extension table from their own chosen reference sequence and with their own chosen settings. Accordingly, a recipient of the hash table and seed extension builder installation package can build their own hash table at any time from their chosen reference, store it on disk, load it into a memory 180 accessible to a programmable circuit 162 and execute mapping and aligning using the programmable circuit 162.

FIG. 2 is a flowchart of a process 200 for generating a hash table index that facilitates flexible seed extension for hash table genomic mapping. In general, the process 200 can include obtaining, by a computer system, a particular seed of nucleotides from a reference sequence, the particular seed representing a sequence of nucleotides having a nucleotide length of K nucleotides (210), determining, by the computer system, that the particular seed matches more than a predetermined number of reference sequence locations (220), based on determining that the particular seed matches more than a predetermined number of reference sequence locations, generating, by the computer system, a seed extension tree having a plurality of nodes, wherein each node of the plurality of nodes corresponds to (i) an extended seed that is an extension of the particular seed and has a nucleotide length of K*, wherein K* is one or more nucleotides greater than K, and (ii) a plurality of locations, in a seed extension table, that include data describing reference sequence locations that match the extended seed (230), and for each node of the plurality of nodes: storing, by the computer system, interval information at a location of the hash table that corresponds to an index key for the extended seed, wherein the interval information references a plurality of locations, in the seed extension table, that include data describing reference sequence locations that match the extended seed associated with the node (240), thereby generating the hash table. The process 200 will be described in further detail below as being performed by a computer system such as a computer 110.

In more detail, a computer system can begin performance of the process 200 by obtaining, by a computer system, a particular seed of nucleotides from a reference sequence, the particular seed representing a sequence of nucleotides having a nucleotide length of K nucleotides (210). In some implementations, obtaining a particular seed can include determining, by the computer system, a location of a seed access window within a reference sequence. The computer system can then obtain a subset of the reference sequence that is identified by the seed access window. The computer system can include one or more computers.

The computer system can continue performance of the process 200 by determining, by the computer system, whether the particular seed matches more than a predetermined number of reference sequence locations (220). If it is determined, by the computer system, that the particular seed does not match more than the predetermined number of references sequence locations, the computer system can determine not to generate a seed extension tree for the particular seed. Instead, the computer system can obtain data describing each of the reference sequence locations that match the second seed. Then, the computer system can store the data describing the reference sequence locations that match the particular seed at a second location of the hash table that corresponds to an index key for the particular seed.

Alternatively, if it is determined, by the computer system, that the particular seed matches more than a predetermined number of reference sequence locations, the computer system can generate a seed extension tree having a plurality of nodes (230). Each node of the plurality of nodes can include data representing (i) an extended seed that is an extension of the particular seed and has a nucleotide length of K*, wherein K* is one or more nucleotides greater than K, and (ii) a plurality of locations, in a seed extension table, that include data describing reference sequence locations that match the extended seed. In some implementations, the plurality of locations can include a contiguous interval, in an extension table, of reference sequence locations that match the extended seed associated with the node.

The computer system can continue performance of the process 200 by storing, for each node of the seed extension tree, interval information in hash locations of the hash table. In some implementations, the computer system can store the interval information, for each node of the seed extension tree, at a hash location of the hash table that corresponds to an index key for the extended seed, thereby generating the hash table (240). The interval information can include references to a plurality of seed extension locations that include data describing reference sequence locations that match the extended seed associated with the node. In some implementations, the plurality of seed extension table locations described by the interval information can include a contiguous interval of locations, in the seed extension table, that include data describing reference sequence locations that match the extended seed.

Runtime Flexible Seed Extension Using Hash Table Genomic Mapping

FIG. 3 is a contextual diagram of a run-time system 300 for performing run-time flexible seed extension for hash table genomic mapping. The run-time system 300 includes a programmable logic circuit 162, a mapping and aligning unit 170, a hash table 140, a memory 18, and multiple seed extension tables such as seed extension table 132 stored in the memory 180. Though the example of FIG. 3 describes a mapping and aligning unit 170 and a hash table 140 implemented in hardware using hardware logic circuits of the programmable logic unit 162, the present disclosure is not so limited. Instead, the mapping and aligning unit 170 may be a software application implemented using software instructions executed by one or more CPUs, GPUs, or a combination thereof, that accesses the hash table 140 stored in a memory unit.

Performance, by the system 300, of run-time flexible seed extension for hash table genomic mapping can begin by the mapping and aligning unit 170 accessing a current read 305. The current read 305 can be generated by a nucleic acid sequencer that has performed primary analysis of a biological sample. Primary analysis can include receiving, by the nucleic acid sequencer, a biological sample such as a blood sample, tissue sample, or sputum, and generating output data such as one or more reads 305 that represents an order of nucleotides in nucleic acid sequences in the received biological sample. In some implementations, the biological sample can include a DNA sample and the nucleic acid sequencer can include a DNA sequencer. In such implementations, the order of sequenced nucleotides in a read 305 generated by the nucleic acid sequencer can include one or more of guanine (G), cytosine (C), adenine (A), and thymine (T) in any combination. In other implementations, the nucleic acid sequencer can include an RNA sequencer, and the biological sample can include an RNA sample. In such implementations, the order of sequenced nucleotides in a read generated by the nucleic acid sequencer can include one or more of G, C, A, and uracil (U) in any combination. Accordingly, though the example of FIG. 3 describes processing of a read comprised of G, C, A, and T that is generated by a DNA sequencer based on a DNA sample, the present disclosure is not so limited. Instead, other implementations can process reads comprised of C, G, A, and U that are generated by an RNA sequencer based on an RNA sample.

In general, the mapping and aligning unit 170 can be configured to be agnostic to the type of read that it receives, maps, and aligns. For example, in some implementations, the same binary code can be used to represent 'T' and 'U'. Reads received by the mapping and aligning unit 170 can include DNA, cDNA, and/or RNA, and the reference can be DNA, cDNA, and/or RNA. In such implementations, read bases T and/or U can share a single binary code so that read Ts and/or Us are matched to reference Ts and/or Us.

In some implementations, the nucleic acid sequencer can include a next generation sequencer (NGS) that is configured to generate sequence reads such as read 305 for a given sample in a manner that achieves ultra-high throughput, scalability, and speed through the use of massively parallel sequencing technology. The NGS enables rapid sequencing of whole genomes, the ability to zoom into deeply sequenced target regions, utilize RNA sequencing (RNA-Seq) to discover novel RNA variants and splice sites, or quantify mRNAs for gene expression analysis, analysis of epigenetic factors such as genome-wide DNA methylation and DNA-protein interactions, sequencing of cancer samples to study rare somatic variants and tumor subclones, and studying of microbial diversity in humans or in the environment.

The sequence reads such as read 305 generated by the nucleic acid sequencer can be accessed, and processed, by a secondary analysis unit such as a mapping and aligning unit 170. In some implementations, the secondary analysis unit such as the mapping and aligning unit 170 can be implemented in hardware, such as digital logic circuits, using a programmable circuit 162 such as a Field Programmable Gate Array (FPGA) or Application Specific Integrated Circuit (ASIC). In other implementations, the secondary analysis unit such as the mapping and aligning unit 170 can be implemented using one or more CPUs, GPUs, or a combination of both, to implement the functionality of the mapping and aligning unit 170. While the hash table 140 can be implemented in hardware logic circuits of the programmable circuit 162 in some implementations such as where the mapping and aligning unit 170 is implemented using the programmable circuit 162, the present disclosure is not so limited. Instead, the hash table 140 can be stored in a memory device and accessed when needed by (i) a CPU, GPU, or combination of both, executing software instructions that realize the functionality of the mapping and aligning unit 170 or (ii) a mapping and aligning unit 170 that has been implemented in hardware digital logic circuits.

In some implementations, the programmable circuit 162 can be integrated with the nucleic acid sequencer that generated the read 305. In such implementations, for example, the programmable circuit 162 can be housed in an expansion card such as a Peripheral Component Interconnect (PCI) expansion card and installed into the nucleic acid sequencer. In other implementations, for example, each of the programmable circuit 162 can be part of another computer that is different than the nucleic acid sequencer and directly connected to the nucleic acid sequencer using an Ethernet cable, a USB cable, a USB-C cable, or the like. In yet other implementations, for example, the programmable circuit 162 can be integrated into a cloud-based server that is remotely accessible by the nucleic acid sequencer that generated the read 305 using one or more wired or wireless networks such as local area network (LAN), a wide area network (WAN), a cellular network, the Internet, or a combination thereof.

The mapping and aligning unit 170 can receive a first hash query 310 that includes an initial seed "GTTTA" 310*a*. In some implementations, a hash query can merely be comprised of a seed of a sample read such as current read 305 that is used as an input to the hash table 140. In other implementations, additional data, metadata, or the like may be added to the seed of the sample read to translate the sample read into a format that can be used to search the hash table 140.

In the example of FIG. 3, the initial seed "GTTTA" 310*a* included in the hash query 310 is obtained from a first portion of the current read "ACGTTTAGC" 305 that is identified using a seed access window 305*a*. The mapping and aligning unit 170 can execute the hash query 310 using the hash table 140 to map the initial short seed 310*a* to a hash location 144 using the hash function 143. In the example of FIG. 3, the execution of the hash query 310 determines that the seed "GTTTA" 310*a* matches the hash index key "GTTTA" 142-2, which is mapped to the hash location 144-*y* by the hash function 143.

The mapping and aligning unit 170 can generate a response 310*b* to the hash query 310 using the hash table 140. The response 310*b* can include the contents of the hash location 144-*y* that is reached by the seed 310*a* of the hash query 310. The mapping and aligning unit 170 evaluate the response 310*b* to the hash query 310 and determine whether the contents include a set of matching reference sequence locations, an extend record, an interval record, or a combination thereof. If the response 310*b* only includes a set of matching reference sequence locations without an extend record or interval record, the mapping and aligning unit 170 can store the set of matching reference sequence locations in the seed match set 352 along with metadata that associates the matching reference locations with the seed of the received query. Alternatively, if the mapping and aligning unit 170 determines that the response includes an interval record, an extend record, or both, the mapping and aligning unit 170 must determine 320 whether to use the matching reference seeds identified by the interval record or proceed with extension of the seed of the query.

In the example of FIG. 3, evaluation of the response 310*b* indicates that (i) the response does not include a set of matching reference sequence locations and (ii) that the response 310*b* includes an extend record 153*a* and an interval record 153*b*. Based on the response 310*b*, the mapping and aligning unit 170 can determine 320 whether the matching reference locations identified by the interval record 153*b* are to be accessed. In some implementations, the mapping and aligning unit 170 will not access the matching reference sequence locations identified by an interval record such as interval record 153*b* if the response such as 310*b* to a hash query 310 includes an extend record 153*a*.

In other implementations, however, the mapping and aligning unit 170 can be configured to evaluate the number of matching reference sequence locations identified by an interval record 153*b* prior to extending the seed 310*a* using the extend record 153*b*. In such implementations, if the number of matching reference sequence locations falls below a predetermined threshold, then the mapping and aligning unit 170 can output 310*d* the matching reference sequence locations at interval A identified by the interval record. Outputting the matching reference sequence locations can include accessing, by the mapping and aligning unit 170, the matching reference sequence locations stored at interval A of the seed extension table 132 in the memory 180 and storing the accessed matching reference sequence locations in seed match set storage 352. Once the accessed matching reference sequence locations are stored in the seed match set 352, the process described by FIG. 3 could end, without further extension of the seed 310*a*. Then, the seed access window 305*a* could be adjusted forward one or more nucleotides along the current read 305. Once the seed access window 305*a* is adjusted, the process described with respect to FIG. 3 can begin again and iteratively continue until the entirety of the current read 305 has been queried. On the other hand, in this alternative implementation, if it was determined that the number of matching reference sequence locations does not fall below the predetermined threshold, then the seed 310*a* can be extended using the extend record 152*a*.

Back to the example of FIG. 3, the mapping and aligning unit 170 does not apply the aforementioned thresholds to the matches identified by the interval record 153*b*. Instead, the mapping and aligning unit 170 determines 320 not to use the matching reference sequence locations identified by the interval record 153*b* because the output 310*b* includes an extend record 153*a*. Accordingly, in this scenario, the mapping and aligning unit 170 determines to extend the seed 310*a*.

Before proceeding to execute subsequent query based on the extended seed, the mapping and aligning unit can store information describing interval A 310*c* in "best interval" storage 350. Interval A can be considered a "best interval" of matching reference sequence locations in the seed extension table 132 for the seed 310*a*, because no other intervals have been identified and evaluated at this point in the process. In subsequent iterations of the process described by FIG. 3, however, each subsequent interval that is identified can be heuristically evaluated to determine whether the interval is better than the existing interval stored in best interval storage for the initial seed 310*a*, or its extended seeds. Storing information describing interval A 310*c* in best interval storage 340 enables the matching reference sequence locations at interval A to be revisited in the event extension of initial seed 310*a* causes a mapping failure such as an unread mapped problem or a high-confidence mapping problem. Information describing the interval A 310*c* can include data describing a start location and an end location of a contiguous list of reference sequence locations that match the initial seed. In some implementations, the information describing the interval A 310*c* can also include data identifying the seed to which the reference sequence locations identified by the interval A match.

Performance of flexible seed extension by the mapping and aligning unit 170 can continue with the mapping and aligning unit 170 generating a first extended seed 312*a* that is an extension of the initial seed 310*a* using the extend record 153*a*. In the example of FIG. 3, the extend record 153*a* can include one or more instructions that instruct the mapping and aligning unit 170 to symmetrically extend the initial seed 310*a* by two bases or nucleotides. In the example of FIG. 3, symmetrically extending the initial seed "GTTTA" 310*a* by two bases or nucleotides results in an extended seed "CGTTTAG" 312*a* of read 305. In some implementations, the additional nucleotides "C" and "G" used to extend the initial seed 310*a* can be obtained from the next nucleotides of the read 305 on opposite sides of the initial seed 310*a* identified by the seed access window 305*a*.

Though there is an additional seed on each side of the seed access window to facilitate this seed extension, in other implementations, such as when the seed access window is at the beginning of a read 305, an extension may cause extension of the initial seed beyond the boundaries of read 305. In such implementations, seed extension can fail and the process of mapping the initial seed to matching reference sequence locations using the hash table 140 can terminate without any matching reference sequence locations being added to the seed match set 352 for the query cycle that began with the initial seed. However, in such implementations, the seed access window 305*a* can be adjusted one or more nucleotides forward along the read 305 and a next seed of the read 305 identified by the adjusted seed access window can be obtained for use as an initial seed of a hash query for a new query cycle using the hash table 140. Execution of the new query cycle for the next seed, and each of seeds thereafter until each of the seeds of read 305 have been processed can be used to update a best interval storage 350, store one or more sets of matching reference sequence locations in a seed match set storage 352, or both, which can be evaluated to identify an optimal set of matching reference sequence locations for the read 305 as described with reference to FIG. 5 despite the failed seed extension, thus solving unmapped read problems which can exist in conventional methods.

Similar seed extension failures can happen for similar reasons as the seed access window 305*a* advances towards the opposed ends of the read 305. The present disclosure similarly solves these seed extension failures by evaluating the best interval storage 250, seed match sets 353, or both, from prior iterations of hash queries for the read as described with reference to FIG. 5.

Back to the example of FIG. 3, the mapping and aligning unit 170 can generate a subsequent hash query 312 that includes the first extended seed 312*a*. The mapping and aligning unit 170 can obtain the first extended seed 312*a* from the hash query 312 and use the hash table to map the first extended short seed 312*a* to a hash location 144 using the hash function 143. In some implementations, generation of a hash query 312 using the first extended seed 312*a* can include providing the first extended seed 312*a* to the mapping and aligning unit 170 as an input for seed mapping using the hash table 140 without the generation of a query. In the example of FIG. 3, the execution of the hash query 312 determines that the seed "CGTTTAG" 312*a* matches the hash index key "CGTTTAG" 142-*x*, which is mapped to the hash location 144-3 by the hash function 143.

The mapping and aligning unit 170 can generate a response 312*b* to the hash query 312 using the hash table 140. The response 312*b* can include the contents of the hash location 144-3 that is reached by the seed 312*a* of the hash query 312. The mapping and aligning unit 170 can evaluate the response 312*b* to the hash query 312 and determine that response 312*b* (i) does not include a set of matching reference sequence locations and (ii) includes an extend record 152*a* and an interval record 152*b*. Based on the response 312*b*, the mapping and aligning unit 170 can determine 330 whether the matching reference locations identified by the interval record 152*b* are to be accessed. In some implementations, the mapping and aligning unit 170 will not access the matching reference sequence locations identified by an interval record such as interval record 152*b* if the response such as 312*b* to a hash query 312 includes an extend record 152*a*.

In other implementations, however, the mapping and aligning unit 170 can be configured to evaluate the number of matching reference sequence locations identified by an interval record 152*b* prior to extending the seed 312*a* using the extend record 152*b*. In such implementations, if the number of matching reference sequence locations identified by interval record 152*b* falls below a predetermined threshold, then the mapping and aligning unit 170 can output 312*d* the matching reference sequence locations at interval B identified by the interval record 152*b*. Outputting the matching reference sequence locations can include accessing, by the mapping and aligning unit 170, the matching reference sequence locations stored at interval B of the seed extension table 132 in the memory 180 and storing the accessed matching reference sequence locations in seed match set storage 352. Once the accessed matching reference sequence locations are stored in the seed match set storage 352, the process described by FIG. 3 could end, without further extension of the seed 312*a*. Then, the seed access window 305*a* could be adjusted one or more nucleotides along the current read 305. Once the seed access window 305*a* is adjusted, the process described with respect to FIG. 3 can begin again and iteratively continue until the entirety of the current read 305 has been queried. On the other hand, in this alternative implementation, if it was determined that the number of matching reference sequence locations does not fall below the predetermined threshold, then the seed 312*a* can be extended using the extend record 152*a*.

Back to the example of FIG. 3, the mapping and aligning unit 170 does not apply the aforementioned threshold to the matches identified by the interval record 152*b*. Instead, the mapping and aligning unit 170 determines 330 not to use the matching reference sequence locations identified by the interval record 152*b* because the output 312*b* includes an extend record 152*a*. Accordingly, the mapping and aligning unit 170 determines to extend the seed 312*a*.

Before proceeding to execute a subsequent query based on the extended seed, the mapping and aligning unit can determine whether to store information describing interval B 312*c* as a "best interval" in best interval storage 350. Determining whether to store information describing interval B 312*c* as a "best interval" includes heuristically determining whether the interval B is a better interval than the interval currently stored in best interval storage 352 for the prior iteration of the first extended seed, which in this example is interval A. In one implementation, a best interval from among multiple intervals can be determined by evaluating a number of target hits returned for each interval. In such implementation, a "best" interval can be selected according to a multipart rule. By way of example, the mapping and aligning unit 170 can assign first priority to an interval that contains at least a predetermined number of matching reference sequence locations, which can be referred to by a threshold such as intvl-target-hits(32) matches. However, if each interval has fewer than intvl-target-hits(32) matches, then the interval having the most matches is stored as the best interval. Further, the mapping and aligning unit 170 can assign a second priority to an interval associated with a longer extended seed, as such intervals can be preferred. Moreover, if the mapping and aligning unit 170 determines that at least one interval has at least intvl-target-hits(32) matches, then among all intervals satisfying at least intvl-target-hits(32) matches, a best interval is selected based on the interval that is associated with a longest extended seed. Though the example here refers to a threshold intvl-target-hits(32) having 32 matches, the present disclosure need not be so limited. Instead, the threshold intvl-target-hits( ) can be sent to any number of matching reference sequence locations to implement this multi-part heuristic rule.

In the example of FIG. 3, the interval A, previously stored as a best interval in best interval storage 350, identifies six matching reference sequence locations 132-1 to 132-6 and the interval B identifies three matching reference sequence locations 132-4 to 132-6. Applying an exemplary intvl-target-hit(10) threshold of ten matches, the mapping and aligning unit 170 can apply the multi-part heuristic rule and determine that neither interval satisfies the intvl-target-hit (10) threshold. Thus, in accordance, with the multi-part heuristic rule, the mapping and aligning unit 170 can select the interval A as the best interval because interval A has the most matches, i.e., six, between interval A and interval B. Based on application of this exemplary multi-part heuristic rule, information describing interval B 321*c* can be discarded and interval A remains stored as the best interval. However, under other examples that apply a different heuristic rule, which need not be a multi-part heuristic rule, it is possible for interval B to be selected as a best interval and stored in best interval storage 350 to replace interval A. Such outcomes can ultimately be left to particular design configurations such as setting of the intvl-target-hits( ) threshold, design of one or more heuristic rules, or the like.

In the example of FIG. 3, the aforementioned heuristic rule is used to compare an interval A previously stored in best interval storage 350 and an interval B that is included in a response 312*b* to a query 312. However, the present disclosure need not be so limited. For example, in some implementations, a response to a hash query may include multiple interval records that were stored in a hash location 144 that is reached by a particular seed of a hash query. In such implementations, the mapping and aligning unit 170 can apply the aforementioned heuristic rules to determine which of the multiple interval records should be accessed. Likewise, the mapping and aligning unit 170 can also use such heuristic rules to determine a best interval, for storage in best interval storage 450, from amongst each of the interval records returned in the query response. By way of another example, the mapping and aligning unit 170 can also use such heuristic rules to determine a best interval, for storage in best interval storage 450, from amongst each of the interval records returned in the query response and another interval previously stored in best interval storage 350 for the prior iteration of the seed used in the query returning multiple intervals.

In some implementations, the system 300 can facilitate storage of more than one best interval in the best interval storage 350. For example, in some implementations up to 2 best intervals may be tracked. In some implementations, up to N best intervals may be tracked. In such implementations, if N>1 best intervals are stored, the criteria for determining which intervals are retained can involve an evaluation of relationships between or among the candidate intervals, their associated extended seeds, or both, such as requiring that the N best intervals are associated with extended seeds that do not overlap each other within the read.

Performance of flexible seed extension by the mapping and aligning unit 170 can continue with the mapping and aligning unit 170 generating a second extended seed 314*a* that is an extension of the first extended seed 312*a* using the extend record 152*a*. In the example of FIG. 3, the extend record 152*a* can include one or more instructions that instruct the mapping and aligning unit 170 to symmetrically extend the first extended seed 312*a* by two bases or nucleotides. In the example of FIG. 3, symmetrically extending the first extended seed "CGTTTAG" 312*a* by two bases or nucleotides results in a second extended seed "ACGTTTAGC" 314*a* of read 305. In some implementations, the additional nucleotides "A" and "C" used to extend the first extended seed 312*a* can be obtained from the next nucleotides of the read 305 on opposite sides of the first extended seed "CGTTTAG" 312*a*.

Back to the example of FIG. 3, the mapping and aligning unit 170 can generate a subsequent hash query 314 that includes the second extended seed 314*a*. The mapping and aligning unit 170 can obtain the second extended seed 314*a* from the hash query 314 and use the hash table to map the second extended short seed 314*a* to a hash location 144 using the hash function 143. In some implementations, generation of a hash query 314 using the second extended seed 314*a* can include providing the second extended seed 314*a* to the mapping and aligning unit 170 as an input for seed mapping using the hash table 140 without the generation of a query. In the example of FIG. 3, the execution of the hash query 314 determines that the seed "ACGTTTAGC" 314*a* matches the hash index key "ACGTTTAGC" 142-1, which is mapped to the hash location 144-2 by the hash function 143.

The mapping and aligning unit 170 can generate a response 314*b* to the hash query 314 using the hash table 140. The response 314*b* can include the contents of the hash location 144-2 that is reached by the second extended seed 314*a* of the hash query 314. The mapping and aligning unit 170 evaluate the response 314*b* to the hash query 314 and determine that response 314*b* (i) includes a set of matching reference sequence locations 155, (ii) does not include an extend record, and (iii) does not include an interval record. Based on the response 314*b*, the mapping and aligning unit 170 can determine that the matching reference sequence locations 155 should be stored in the seed match set storage 352.

Because the response 314*b* does not include an extend record, the runtime flexible seed extension process for the seed "GTTTA" 310*a* of the read 305 ends. The seed access window 305*a* can continue to be advanced one or more nucleotides along the read 305 until each the process described with respect to FIG. 3 is performed on each respective seed of the read 305. This process is also described with respect to the flowchart of FIG. 4. As described above, as the seed access window 305*a* extends towards the end of read 305, attempts to extend a seed input to the mapping and aligning unit 170 can fail, creating a potential unmapped read problem. However, the present disclosure can use one or more intervals stored in the best interval storage, one or more reads stored in the seed match set 352, or a combination of both, to identify a set of matching reference sequence locations for the read 305 as described with respect to at least FIG. 5.

FIG. 4 is a flowchart of a process 400 for performing run-time flexible seed extension for hash table genomic mapping. The process 400 will be explained below as being performed by a computer system of one or more computers. The one or more computers can include, for example, a mapping and aligning unit 170. For purposes of this disclosure, the one or more computers can include a CPU or GPU that is configured to obtain and execute software instructions to realize particular programmed functionality described by the software instructions. Alternatively, or in addition, the one or more computers can include a programmable circuit that has been configured so that hardware digital logic circuits of the programmable circuit have been configured to realize particular programmed functionality in hardware.

The computer system can begin performance of the process 400 by executing a query of a hash table 405. The query can include a seed of nucleotides. The seed of nucleotides can include a subset of nucleotides that were obtained from a read. The read can include a set of nucleotides generated by a nucleic acid sequencer based on a biological sample that was input into the nucleic acid sequencer. The biological sample can include, for example, a blood sample, tissue sample, sputum, or the like.

By way of example, a read generated by the nucleic acid sequencer based on a biological sample can include a series of nucleotides such as "ACGTTTAGC." This example includes a read of 9 nucleotides. However, use of a read of 9 nucleotides is only used as an example. Instead, of being limited to 9 nucleotides, reads as described by the present disclosure can be of any nucleotide length including, but not limited to, 5 bases or nucleotides, 10 bases or nucleotides, 12 bases or nucleotides, 15 bases or nucleotides, 18 bases or nucleotides, 21 bases or nucleotides, 25 bases or nucleotides, 35 bases or nucleotides, 50 bases or nucleotides, 100 bases of nucleotides, 150 bases or nucleotides, 1,000 bases or nucleotides, 1,000,000 bases or nucleotides, or even more bases or nucleotides. The seed of the query can include a portion of the read such as "GTTTA." A seed obtained from the read for use in a first hash query during a first iteration of the process 400 can be of any length K, where K is less than the number of bases or nucleotides in the read. In some implementations, K can be substantially less than the read nucleotide length such as 1/100$^{th}$ of the read length, 1/10$^{th}$ of the read length 1/5$^{th}$ of the read length, or the like.

The computer system can execute a query that includes the seed by obtaining the seed and comparing the seed to hash keys of the hash table. The hash keys can correspond to each reference sequence seed, a reverse complement of each reference sequence seed, each extended seed of the reference sequence, and a reverse complement of each extended seed of the reference sequence. A reference sequence can include, for example, a reference genome, or a portion thereof, for a species such as a human or other animal. When a hash key that matches the seed of the query is identified by the computer system, the computer system can use a hash function to map the hash key to one or more hash locations. In some aspects of the present disclosure, one or more hash locations can store (i) an extend record, (ii) an interval record, or (iii) one or more reference sequence locations. The computer system can generate a response to the query that includes the contents of the one or more hash locations that were reached by the seed of the query.

The computer system can continue performance of the process 400 by obtaining a response to the executed query that includes information stored by the one or more locations of the hash table that are determined to be reached by the query (410). The one or more locations of the hash table are determined to be reached by the query if the seed of the query is determined to match a hash key that is mapped to the one or more locations using a hash function.

The computer system can continue performance of the process 400 by determining whether the response to the executed query includes (i) an extend record (ii) an interval record, or (iii) one or more matching reference sequence locations (415). Determining, by the computer system, whether the response to the executed query includes (i) an extend record (ii) an interval record, or (iii) one or more matching reference sequence locations (415) can include parsing the received response and analyzing the parsed response data. The computer system can determine, based on the parsed data, whether the parsed data represents (i) an extend record, (ii) an interval record, or (iii) one or more matching references sequence locations. In other implementations, the response to the executed query may include one or more data flags that indicate whether the response includes (i) an extend record, (ii) an interval record, or (iii) one or more matching reference sequence locations.

In some instances, the computer system can continue performance of the process 400 by determining, at stage 415, that the response does not include an extend record, an interval record, or one or matching reference sequence locations. If the computer system determines that the response does not include (i) an extend record, (ii) an interval record, or (iii) one or more matching reference sequence locations, then the process ends at stage 420 without adding any matching reference sequence locations to a seed match set for the seed of the query. By way of example, the obtained response to the query that includes the seed may not include (i) an extend record, (ii) an interval record, or (iii) one or more matching references sequence locations if the seed is an extended seed and there was a seed extension error. Such a seed extension error may exist, for example, if the computer system attempts to extend the seed beyond an end of the read from which the seed was obtained.

Alternatively, in other instances, the computer system can continue performance of the process 400 by determining, at stage 415, that the response to the executed query includes an (i) extend record, (ii) an interval record, or (iii) both. In such instances, the computer system can continue performance of process 400 by determining whether an extension table is to be accessed to obtain one or more matching reference sequence locations in the extension table that are referenced by the interval record (430).

In some instances, the computer system can continue performance of the process 400 by determining that the seed extension table is to be accessed to obtain one or more matching reference sequence locations in the extension table that re referenced by the interval record. For example, in some implementations, the computer system can be configured to access a seed extension table to obtain one or more matching references sequence locations identified by the interval record if the number of matching reference sequence locations falls below a predetermined threshold. Alternatively, or in addition, the computer system can be configured to access a seed extension table to obtain one or more matching reference sequence locations identified by the interval record if the response to the executed query also included a "STOP" record that was stored at the hash location reached by the seed of the hash query. The "STOP" record can instruct the computer system to not perform any further seed extensions of the seed in the query and access the one or more matching reference sequence locations identified by the interval record, preferentially, such as if the number of matching reference sequence locations falls below a predetermined threshold.

In such instances, where the computer system determines at stage 430 that the seed extension stable is to be accessed, the computer system can continue performance of the process 400 by accessing the seed extension table to obtain the one or more reference sequence locations in the seed extension table (450). The computer system can identify a particular set of one or more matching reference sequence locations to obtain from the seed extension table by using the interval record. The interval record can include information that references a plurality of locations, in the seed extension table, that include data describing reference sequence locations that match the seed of the query. In some implementations, the information that references the plurality of locations can include a contiguous interval, in the extension table, of reference sequence locations that match the extended seed of the query. Alternatively, in other implementations, the information that references the plurality of locations can include one or more non-contiguous intervals, in the extension table, of reference sequence locations that match the seed of the query.

In such instances, the computer system can obtain the one or more matching reference sequence locations from the seed extension table that are identified using the interval record. The obtained one or more reference sequence locations can be added to a seed match set (455). In some implementations, adding the one or more matching reference sequence locations to the seed match set can include obtaining and storing data representing the one or more matching reference sequence locations in a location of a memory device allocated for seed match set storage. In other implementations, adding the one or more matching reference sequence locations to the seed match set can include storing data, such as a pointer, that references the interval(s) of the seed extension table storing the one or more reference sequence locations. Accordingly, the seed match set can be a storage location that stores a set of identified and obtained matching reference sequence locations. Alternatively, the seed match set can include one or more storage locations that store references to the one or more matching reference sequence locations. The computer system can end this instance of process 400 at 460 upon addition of the one or more matching reference sequence locations, identified by the interval record, to the seed match.

In other instances, after the computer system determines (415) that the response includes at least (i) an extend record, (ii) an interval record, or (iii) or both, the computer system can determine (430) that the seed extension table is not to be accessed to obtain one or more matching reference sequence locations. The determination, by the computer system, that the seed extension table is not to be accessed to obtain one or more matching reference sequence locations may be based on a variety of factors. By way of example, in some implementations, the computer system can determine not to access the seed extension table to obtain matching reference sequence locations identified by an interval record if the response returned an extend record. Such a determination can be preferred, because the extended seed is likely to yield a smaller set of matching references sequence locations than the set of matching reference sequence location identified by the interval record.

By way of another example, in other implementations, the computer system can determine not to access the seed extension table to obtain matching reference sequence locations identified by an interval record if the computer system determines that the number of matching reference sequence locations exceeds a predetermined threshold number of matching reference sequence locations. Similarly, in such implementations when the match threshold is exceeded by the matching reference sequence locations identified by the interval, the computer system can determine not to access the seed extension table.

When the computer system determines 430 not to access the seed extension table, the computer system can continue performance of the process 400 by determining 465 whether the obtained response includes an interval record and an extend record. If the computer system determines 465 that the obtained response includes an interval record and an extend record, then the computer system can determine 435 whether to store the interval record, or information describing the interval record, included in the response to the executed query as a candidate best interval. During a first iteration of the process 400 for a query having an initial seed that has not yet been extended, the computer system can determine to store the interval record, or information describing the interval record, in best interval storage of a memory device as a candidate best interval. Because such interval records are encountered during the initial iteration of the process 400 for a query having an initial seed that has not been extended, no other interval records have been encountered in responses to other queries for one or more subsequent extended seeds. Accordingly, a first interval returned in response to a query having an initial seed that has not yet been extended must be a "best interval," as no other intervals have yet been identified for comparison.

However, for subsequent interactions through the process 400 after a response has been received for a query having an extended seed, the computer system can obtain a second interval record from the response to the query having the extended seed. In such instances, the computer system can heuristically determine whether the second interval record should be used to replace the previously stored candidate best interval in best interval storage. The determination as to whether to keep the previously stored candidate best interval or replace the candidate best interval with the second interval, or information describing the interval, can be made by applying one or more heuristic rules as described with reference to the example of FIG. 3. In some implementations, the heuristic rules can include one or more multi-part heuristic rules.

Though some implementations of the present disclosure can be directed towards iteratively evaluating each subsequently returned interval record versus a previously stored candidate best interval to determine a single best interval that should be stored for a current read on which the seed of the query is based, the present disclosure need not be so limited. Instead, in some implementations, all intervals can be saved in an interval storage and later evaluated for use in supplementing the seed match sets.

The computer system can continue performance of the process 400 by generating an extended seed (440). The extended seed can be generated based on the instructions included in the extend record returned in response to the query. By way of example, the extend record can include one or more instructions that, when executed by a computer such as a central processing unit (CPU) or graphics processing unit (GPU) executing software instructions or programmable circuit 162, can cause the CPU, GPU, or programmable circuit to extend the seed used in the hash query that reached the hash location storing the extend record by one or more nucleotides. In some implementations, an extend record can be generated such that the extend record instructs a computer to extend a seed symmetrically on each end of the seed. Accordingly, by way of example, an extend record can be generated to instruct a computer such as a CPU, GPU, or the programmable circuit 162 to extend a seed by two nucleotides, four nucleotides, six nucleotides, or the like. In such implementations, symmetrical extension of the seed can be achieved by extending the seed by one nucleotide on each respective end of the seed, two nucleotides on each respective end of the seed, three nucleotides on each respective end of the seed, or the like. However, the present disclosure should not be limited to symmetrical extension of seeds. Instead, asymmetrical extension of a seed is also contemplated by the present disclosure.

The computer system can continue performance of the process 400 by generating 445 a hash query that includes the extended seed. The computer system can then perform another iteration of the process 400 by executing the query with the extended query at stage 405 and then continue performance of the process 400 until (a) the process ends at 427 or 460 by added one or more matching reference sequence locations to a seed match set, the process ends at 475 after determining whether to store the interval record as a candidate best interval, or (c) the process ends at stage 420 as the result of one or more errors such as a seed extension error that results in a query that does not receive a response to the executed query that includes (i) an extend record, (ii) an interval record, or (iii) one or more matching reference sequence locations.

Alternatively, if at stage 465 the computer system determines that the obtained response does not include both an interval record and an extend record, then the computer system can continue execution of the process 400 by determining whether the obtained response includes an extend record.

If the computer system determines that the obtained response includes an extend record, the computer system can continue performance of the process 400 by generating an extended seed at stage 440, generating a hash query 445 that includes the extended seed, and performing another iteration of the process 400 by executing the query with the extended query at stage 405. The computer system can then continue performance of the process 400 until (a) the process ends at 427, 420, 460, 475.

If, on the other hand, the computer system determines at stage 467 that the obtained response does not include an extend record, then the computer system can continue performance of the process 400 at stage 470 by determining whether to store the interval record, or information describing the interval record, as a candidate best interval. The computer system can determine whether to store the interval record as a candidate best interval at stage 470 using the same processes described with respect to determining whether to store the interval record as a candidate best interval at stage 435. Regardless of whether the computer system determines to store the interval record as a candidate best interval at stage 470, the process 400 ends at stage 475.

At least one variation of the process 400 can be implemented wherein the computer system determines at stage 470 instead whether the obtained response includes an interval record. In such instances, it logically follows that if the computer system determines that the obtained response includes an interval record, the computer system can continue performance of the process at stage 470. Alternatively, if the computer system determines that the obtained response does not include an interval record, then the process continues at stage 440 by generating an extended seed. Other variations of the process flow of process 400 can be similarly implemented and fall within the spirit and scope of the present disclosure.

Figure 5:
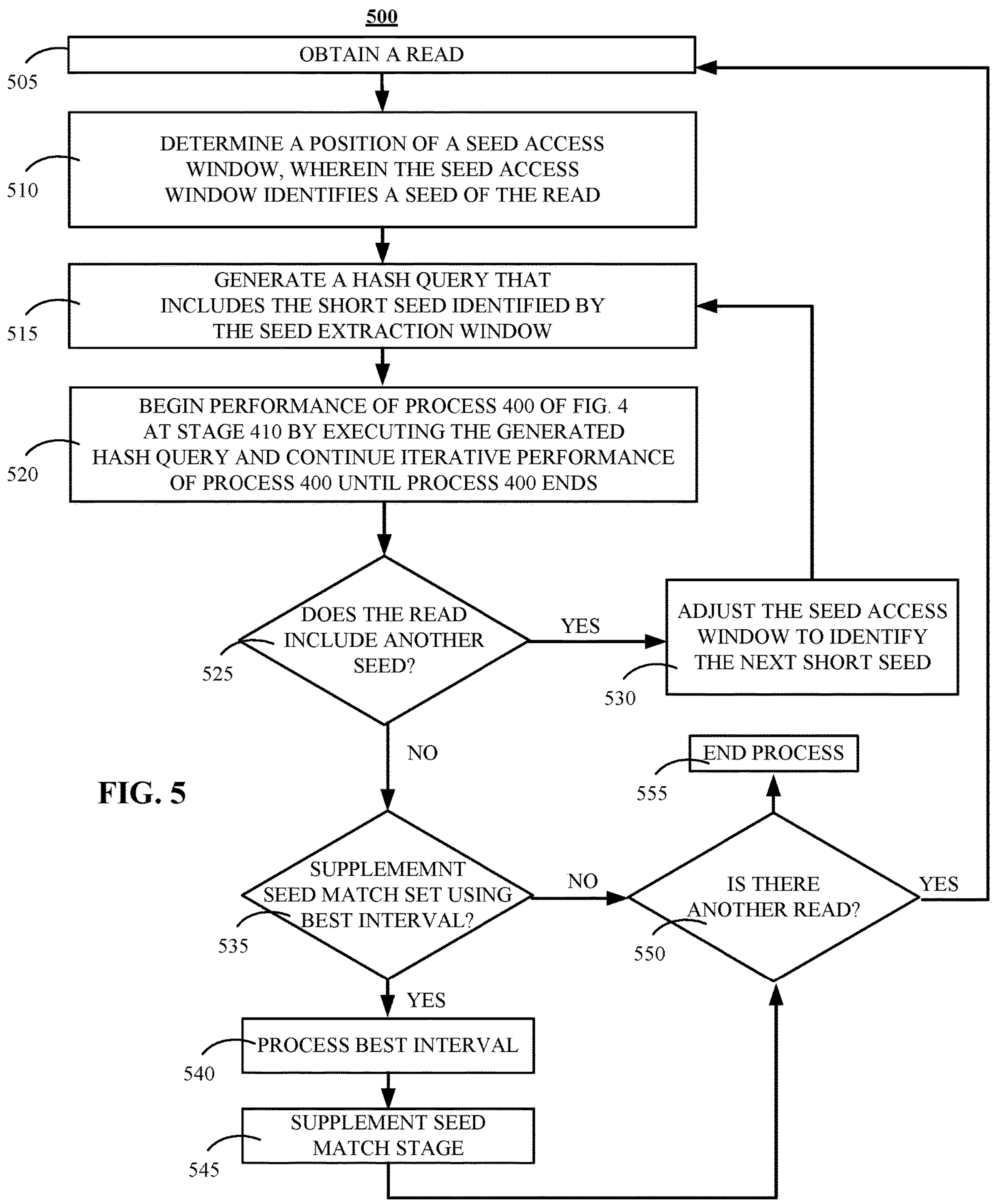
FIG. 5 is a flowchart of a process for performing iterative runtime flexible seed extension for hash table genomic mapping on each seed of a read.

FIG. 5 is a flowchart of a process 500 for performing iterative runtime flexible seed extension for hash table genomic mapping on each seed of a read. In general, the process 500 can include obtaining a read that is generated by a nucleic acid sequencer (505), determining a location of a seed access window, wherein the seed access window identifies a seed of the read (510), generating a hash query that includes the seed identified by the seed access window (515), and beginning performance of the process 400 described by FIG. 4 at stage 410 by executing the generated hash query and continuing iterative performance of the process 400 until the process 400 ends (520), determining whether the read includes another seed (525), and if it is determined that the read includes another seed (525), adjust the seed access window to identify the other seed (530), and perform stage 515 to generate a hash query using the other seed (515).

The process 500 can continue to perform the processing loop of stage 515, 520, 525, and 530 until it is determined at stage 525 that the read obtained at stage 505 does not include another seed to be mapped and aligned using the process 400. In such instances, it can be determined whether to supplement a current seed match set for the read using the best interval (535). If it is determined to use the best interval to supplement the current seed match set at stage 535, the process 500 can continue at stage 540 by processing the best interval (540), supplementing the current seed match set using one or more matching reference sequence locations obtained from a portion of the seed extension table identified using the best interval (545), and determining 550 whether there is another read that is ready for mapping and aligning using the process 500. If there is not another read that is ready for mapping and aligning, then the process 500 ends at stage 555. Alternatively, if there is another read that is ready for mapping and aligning using the process 500, then the process 500 continues at stage 505 by obtaining the other read that is ready for mapping and aligning. The process 500 can then continue to perform the process 500 iteratively until it is determined at stage 550 that there is not another read that is ready for mapping and aligning using the process 500.

The process 500 will be described in more detail below as being performed by a computer system of one or more computers. The one or more computers can include, for example, a mapping and aligning unit 170. For purposes of this disclosure, the one or more computers can include a CPU or GPU that is configured to obtain and execute software instructions to realize particular programmed functionality described by the software instructions. Alternatively, or in addition, the one or more computers can include a programmable circuit that has been configured so that hardware digital logic circuits of the programmable circuit have been configured to realize particular programmed functionality in hardware.

A computer system can begin performance of the process 500 by obtaining data representing a nucleic acid read (also referred to herein as a "read") that is generated by a nucleic acid sequencer (505). The read can be received, by the computer system as input and from the nucleic acid sequencer, after the read is generated by the nucleic acid sequencer. Alternatively, or in addition, a read generated by the nucleic acid sequencer may be stored in a memory device accessible to the computer system. The computer system 500 can then obtain the stored read(s) by accessing the memory to retrieve one or more reads from the memory device. By way of example, a read can include a set of nucleotides such as "ACGTTTAGC." This example includes a read of 9 nucleotides. However, use of a read of 9 nucleotides is only used as an example. Instead, of being limited to 9 nucleotides, reads as described by the present disclosure can be of any nucleotide length including, but not limited to, 5 bases or nucleotides, 10 bases or nucleotides, 12 bases or nucleotides, 15 bases or nucleotides, 18 bases or nucleotides, 21 bases or nucleotides, 25 bases or nucleotides, 35 bases or nucleotides, 50 bases or nucleotides, 100 bases of nucleotides, 150 bases or nucleotides, 1,000 bases or nucleotides, 1,000,000 bases or nucleotides, or even more bases or nucleotides.

The computer system can continue performance of the process 500 by determining a location of a seed access window (510). The seed access window can be used to identify a seed of nucleotides that are comprised of a subset of nucleotides of the read. An example of a seed is the set of sequential nucleotides "GTTTA," which are a seed of the read "ACGTTTAGC." Though the set of sequential nucleotides "GTTTA" represent an example of a contiguous seed of the read "ACGTTTAGC," the present disclosure need not be so limited. Instead, in some implementations, non-contiguous seeds can be obtained and analyzed using the systems and processes described by the present disclosure. For example, a non-contiguous seed such as "G_T_A" can also be obtained from the read "ACGTTTAGC" and analyzed using the systems and methods described here. In such implementations, the systems and methods of the present disclosure may treat the skipped locations represented by an underscore " " as a wildcard that can match any base or nucleotide.

The seed access window can be configured to be of any base or nucleotide length that is less than the read length. The seed access window can be configured to move forward, or backwards, along a sequential read to identify a seed of the read for processing. If non-contiguous seeds are to be utilized, seed access window can be configured accordingly. By way of example, the seed access window can be configured to identify nine nucleotide non-contiguous seeds with a wildcard inserted at nucleotide location 6 and nucleotide location 8.

The computer system can continue performance of the process 500 by generating a hash query that includes the seed identified by the seed access window (515). In some implementations, a hash query can merely be comprised of a seed "GTTTA" of a read such as "ACGTTTAGC." In other implementations, additional data, metadata, or the like may be added to the seed of the sample read to translate the seed into a format that can be used to search the hash table.

The computer system can continue performance of the process 500 by performing the process 400 described by FIG. 4 (520) to map and align the seed of the generated query to one or more reference sequence locations. The computer system begins performance of the process 400 by executing, at stage 410, the hash query generated at stage 515. The computer system can then continue iterative performance of the process 400 until the process 400 terminates at stage 420, 427, 460, or 475, possibly having added matching reference sequence locations to a seed match set at stage 425 or 455.

After the process 400 terminates, the computer system can determine whether the read obtained at stage 505 includes another seed (525). In some implementations, determining whether the read includes another seed include considering all possible seed access window positions in the read. Alternatively, determining whether the read includes another seed can include considering only a predetermined subset of all possible seed access window positions such as only even-numbered seed access window positions or only odd-numbered seed access window positions. Accordingly, the present disclosure does not require that each seed of a read is to be evaluated using the process 500. Instead, in some implementations, they computer system can determine at stage 505 whether there is another seed of a predetermined subset of seeds of a read that is to be evaluated using the process 500.

If the computer system determines that the read includes another seed at stage 525, the computer system can adjust the seed access window to identify the other seed (530), and the computer system can perform stage 515 to generate a hash query using the other seed identified by the adjusted seed access window (515). Adjusting the seed access window can include, for example, moving the seed access window forward along the read obtained at stage 505 by one or more base or nucleotide locations. The computer system can continue performance of the processing loop of stage 515, 520, 525, and 530 until the computer system determines, at stage 525, that the read obtained at stage 505 does not include another seed to be mapped and aligned using the process 400.

Once the computer system determines that the read obtained at stage 505 does not include another seed to be mapped and aligned, the computer system can determine whether to supplement a current seed match set for the read using the best interval (535). In some instances, if the computer system determines that the seed match set should not be supplemented, then the computer system can determine (550) whether there is another read that is ready for mapping and aligning using the process 500. In such instances, if the computing system determines there is another read that is ready for mapping and aligning, the computer system can continue performance of the process 500 at stage 505 by obtaining the other read that is ready for mapping and aligning. The computer system can then iteratively perform the process 500 until it is determined at stage 550 that there is not another read that is ready for mapping and aligning using the process 500.

Alternatively, in other instances, the computer system can determine that the current seed match set for the read should be supplemented using one or more matching reference sequence locations identified by a best interval. The computer system can determine that a current seed match set should be supplemented using one or more matching reference sequence locations identified by the best interval by applying one or more heuristic rules to (i) the seed length of the extended see whose query yielded the best interval, (ii) the seed length of one or more matching reference sequence locations, (iii) a number of seed chains generated, or a combination thereof. In some implementations, the heuristic rules can specify one or more independent triggering conditions that, if triggered, cause the computer system to process the best interval.

By way of example, the first independent triggering condition that can trigger processing, by the computer system, of the best interval is determining whether a seed length of the extended seed whose query yielded the best interval was greater than or equal to intvl-seed-length(60) bases or nucleotides. In this example, the threshold value intvl-seed-length(60) is a predetermined threshold value that can be used, by the computer system, to evaluate the length of extended seeds that yielded the best interval. In this example, the seed length of the extended seed that yielded the best interval that the computer system checks for is sixty nucleotides. However, the present disclosure need not be so limited. Instead, the threshold value intvl-seed-length( ) can be set to any nucleotide length. If the computer system determines that the intvl-seed-length( ) threshold is not satisfied, then the computer system can evaluate the other triggering conditions to determine whether the best interval is to be processed.

By way of another example, the second independent triggering condition that can trigger processing, by the computer system, of the best interval is determining whether a seed length of the extended seed whose query yielded the best interval was larger than the longest matching reference sequence location processed by at least intvl-seed-longer(8) bases or nucleotides. In this example, the threshold value intvl-seed-longer(8) is a predetermined threshold value that can be used, by the computer system, evaluate a comparison of (i) the seed length of the extended seed whose query yielded the best interval and (ii) a longest matching reference sequence locations. In this example, if the computer system determines that a seed length of the extended seed whose query yielded the best interval is eight bases or nucleotides, or more, greater than any matched seed, then processing of the best interval is triggered.

By way of another example, the third independent triggering condition that can trigger processing, by the computer system, of the best interval is determining whether a number of seed chains is less than intvl-min-chains(8). A seed chain can include a group of similarly positioned reference sequence location matches. In this example, the threshold value intvl-min-chains(8) is a predetermined threshold value that can be used to evaluate a number of seed chains generated. In this example, if less than eight seed chains were generated, then the processing of the best interval is triggered.

Though examples of three independent triggering conditions are described for triggering processing of a best interval to supplement a seed match set, the present disclosure need not be so limited. Instead, other triggering conditions can be constructed to trigger processing of a best interval as a particular computer system may require.

If the computer system determines at stage 535 to supplement a seed match set because, for example, a one or more thresholds of a triggering condition for processing a best interval have been satisfied, then the computer system can determine to use the best interval to supplement the current seed match set at stage 535. Using the best interval to supplement the current seed match set can include, the computer system processing the best interval (540). Processing the best interval can include applying one or more heuristic rules to the best interval to identify one or more matching references sequence locations identified by the best interval and stored in a seed extension table.

By way of example, the computer system can determine to process all of the one or more reference sequence locations identified by the best interval if the number of reference sequence location identified by the best interval is less than or equal to intvl-max-hits(64). In this example, if the computer system determines that the best interval identified less than, or equal to, sixty-four matching reference sequence locations, then the computer system can obtain all of the matching reference sequence locations identified by the best interval from a seed extension table using the best interval. Alternatively, if the computer system determines that the best interval identifies more than sixty four matching reference sequence locations, then the computer system can randomly obtain intvl-sample-hits(32) matching references sequence from the set of matching reference sequence locations identified by the best interval.

Randomly obtaining the threshold amount of thirty-two matching reference sequence locations can include randomly, or by deterministic pseudo-random choices, obtaining the threshold amount of thirty-two matching reference sequence locations from a seed extension table using the best interval. The best interval can include data identifying (i) one or more stop and start locations of a seed extension table, (ii) one or more start locations and one or more offsets, or a combination thereof. Though examples of threshold such as sixty-four matching references locations and 32 randomly sampled hits are described, the present disclosure need not be so limited. Instead, other thresholds having other numerical values can be used to achieve the advantages of the present disclosure.

The matching reference sequence locations obtained using the best interval can be used to supplement a current seed match set 545. Such supplementing of the seed match set using the best interval can solve problems such as unmapped read problems or high confidence mismapping problems that may result in no matching references sequence location stored in a seed match set or a very small number of matching reference sequence locations stored in a seed match set, respectively. The matching reference sequence locations may have been, or can be, obtained from the portion of the seed extension table identified by the best interval (540).

Once the seed match set has been supplemented, the computer system can determine whether there is another read that is ready for mapping and aligning using the process 500. If there is another read that is ready for mapping and aligning, then the computer system continues performance of the process 500 by obtaining the other read. Alternatively, if there is not another read that is ready for mapping and aligning, then the process 500 can end at 555.

Note that, in the example described with reference to process 500, a best interval is evaluated to determine whether the best interval, or a portion thereof, can be used to supplement a seed match set. However, there is no requirement that only a single best interval be stored in best interval storage. In some implementations, the computer system can facilitate storage of more than one best interval in the best interval storage. For example, in some implementations up to 2 best intervals may be tracked. In some implementations, up to N best intervals may be tracked. In such implementations, if N>1 best intervals are stored, the criteria for determining which intervals are retained can involve an evaluation of relationships between or among the candidate intervals, their associated extended seeds, or both, such as requiring that the N best intervals are associated with extended seeds that do not overlap each other within the read. In some implementations, the computer system can even select matching reference sequence locations from amongst multiple different best intervals. Such selection of matching reference sequence locations from amongst multiple different best intervals can be performed randomly, pseudo-randomly, or by applying one or more heuristics.

System Components

Figure 6:
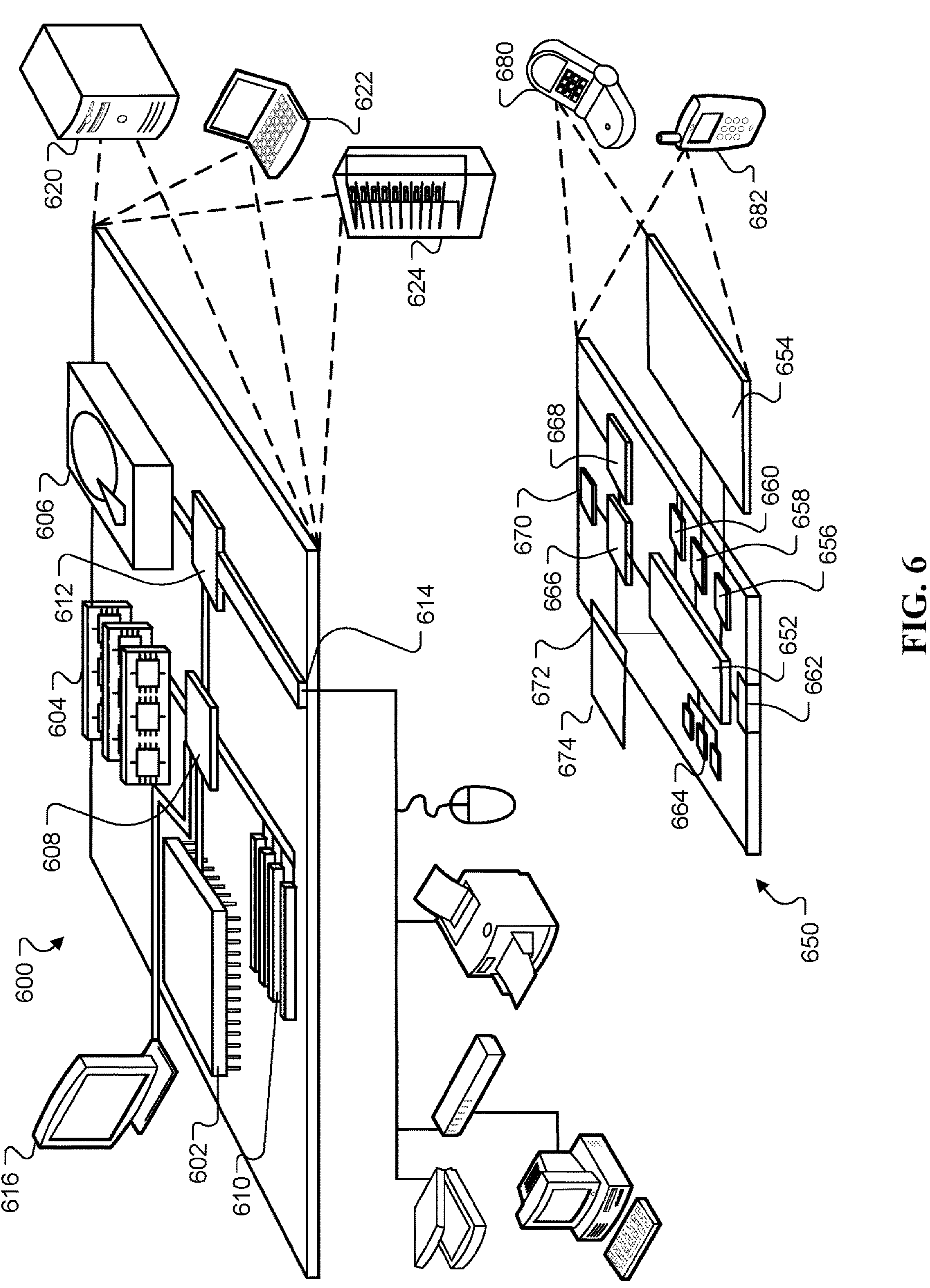
FIG. 6 is a diagram of system components that can be used to implement systems described herein related to flexible seed extensions for hash table genomic mapping.

FIG. 6 is a diagram of system components that can be used to implement systems described herein related to flexible seed extensions for hash table genomic mapping.

Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, and other similar computing devices. Additionally, computing device 600 or 650 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 600 includes a processor 602, memory 604, a storage device 608, a high-speed interface 608 connecting to memory 604 and high-speed expansion ports 610, and a low speed interface 612 connecting to low speed bus 614 and storage device 608. Each of the components 602, 604, 608, 608, 610, and 612, are interconnected using various busses, and can be mounted on a common motherboard or in other manners as appropriate. The processor 602 can process instructions for execution within the computing device 600, including instructions stored in the memory 604 or on the storage device 608 to display graphical information for a GUI on an external input/output device, such as display 616 coupled to high speed interface 608. In other implementations, multiple processors and/or multiple buses can be used, as appropriate, along with multiple memories and types of memory. Also, multiple computing devices 600 can be connected, with each device providing portions of the necessary operations, e.g., as a server bank, a group of blade servers, or a multi-processor system.

The memory 604 stores information within the computing device 600. In one implementation, the memory 604 is a volatile memory unit or units. In another implementation, the memory 604 is a non-volatile memory unit or units. The memory 604 can also be another form of computer-readable medium, such as a magnetic or optical disk.

The storage device 608 is capable of providing mass storage for the computing device 600. In one implementation, the storage device 608 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 604, the storage device 608, or memory on processor 602.

The high-speed controller 608 manages bandwidth-intensive operations for the computing device 600, while the low speed controller 612 manages lower bandwidth intensive operations. Such allocation of functions is only an example. In one implementation, the high-speed controller 608 is coupled to memory 604, display 616, e.g., through a graphics processor or accelerator, and to high-speed expansion ports 610, which can accept various expansion cards (not shown). In the implementation, low-speed controller 612 is coupled to storage device 608 and low-speed expansion port 614. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 600 can be implemented in a number of different forms, as shown in the figure. For example, it can be implemented as a standard server 620, or multiple times in a group of such servers. It can also be implemented as part of a rack server system 624. In addition, it can be implemented in a personal computer such as a laptop computer 622. Alternatively, components from computing device 600 can be combined with other components in a mobile device (not shown), such as device 650. Each of such devices can contain one or more of computing device 600, 650, and an entire system can be made up of multiple computing devices 600, 650 communicating with each other.

The computing device 600 can be implemented in a number of different forms, as shown in the figure. For example, it can be implemented as a standard server 620, or multiple times in a group of such servers. It can also be implemented as part of a rack server system 624. In addition, it can be implemented in a personal computer such as a laptop computer 622. Alternatively, components from computing device 600 can be combined with other components in a mobile device (not shown), such as device 650. Each of such devices can contain one or more of computing device 600, 650, and an entire system can be made up of multiple computing devices 600, 650 communicating with each other.

Computing device 650 includes a processor 652, memory 664, and an input/output device such as a display 654, a communication interface 666, and a transceiver 668, among other components. The device 650 can also be provided with a storage device, such as a micro-drive or other device, to provide additional storage. Each of the components 650, 652, 664, 654, 666, and 668, are interconnected using various buses, and several of the components can be mounted on a common motherboard or in other manners as appropriate.

The processor 652 can execute instructions within the computing device 650, including instructions stored in the memory 664. The processor can be implemented as a chipset of chips that include separate and multiple analog and digital processors. Additionally, the processor can be implemented using any of a number of architectures. For example, the processor 610 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 650, such as control of user interfaces, applications run by device 650, and wireless communication by device 650.

Processor 652 can communicate with a user through control interface 658 and display interface 656 coupled to a display 654. The display 654 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 654 to present graphical and other information to a user. The control interface 658 can receive commands from a user and convert them for submission to the processor 652. In addition, an external interface 662 can be provided in communication with processor 652, so as to enable near area communication of device 650 with other devices. External interface 662 can provide, for example, for wired communication in some implementations, or for wireless communication in other implementations, and multiple interfaces can also be used.

The memory 664 stores information within the computing device 650. The memory 664 can be implemented as one or more of a computer-readable medium or media, a volatile memory unit or units, or a non-volatile memory unit or units. Expansion memory 674 can also be provided and connected to device 650 through expansion interface 672, which can include, for example, a SIMM (Single In Line Memory Module) card interface. Such expansion memory 674 can provide extra storage space for device 650, or can also store applications or other information for device 650. Specifically, expansion memory 674 can include instructions to carry out or supplement the processes described above, and can also include secure information. Thus, for example, expansion memory 674 can be provided as a security module for device 650, and can be programmed with instructions that permit secure use of device 650. In addition, secure applications can be provided via the SIMM cards, along with additional information, such as placing identifying information on the SIMM card in a non-hackable manner.

The memory can include, for example, flash memory and/or Non-volatile random-access memory (NVRAM) memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, or memory on processor 652 that can be received, for example, over transceiver 668 or external interface 662.

Device 650 can communicate wirelessly through communication interface 666, which can include digital signal processing circuitry where necessary. Communication interface 666 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 668. In addition, short-range communication can occur, such as using a Bluetooth, Wi-Fi, or other such transceiver (not shown). In addition, GPS (Global Positioning System) receiver module 670 can provide additional navigation- and location-related wireless data to device 650, which can be used as appropriate by applications running on device 650.

Device 650 can also communicate audibly using audio codec 660, which can receive spoken information from a user and convert it to usable digital information. Audio codec 660 can likewise generate audible sound for a user, such as through a speaker, e.g., in a handset of device 650. Such sound can include sound from voice telephone calls, can include recorded sound, e.g., voice messages, music files, etc. and can also include sound generated by applications operating on device 650.

The computing device 650 can be implemented in a number of different forms, as shown in the figure. For example, it can be implemented as a cellular telephone 680. It can also be implemented as part of a smartphone 682, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

EXAMPLES

The disclosure is further described in the following examples, which do not limit the scope of the claims.

Example 1: Comparing a Percentage of Unmapped Reads Between Systems that Use Flexible Seed Extension and Systems that do not Use Flexible Seed Extension In this example, different nucleic acid sequencers including a HiSeq® 2500 sequencer, a HiSeq® X sequencer, and a NovaSeq® sequencer were used to sequence particular sample. Then, a DRAGEN™ platform was used to map the reads produced by each respective sequencer with flexible seed extension as described herein and without flexible seed extension. Once mapped, a computer system determined a percentage of unmapped reads that resulted from each mapping operations for each sequencer.

The DRAGEN™ platform is a mapping and alignment unit implemented in hardware circuitry of a field programmable gate array (FPGA). The DRAGEN™ v7 platform does not currently utilize flexible seed extension, as described herein, whereas the DRAGEN™ v8 platform does utilize flexible seed extension. Although the DRAGEN™ platforms used herein were implemented in an FPGA, in general, DRAGEN™ platforms can also be implemented in other integrated circuits such as an application specific integrated circuit (ASIC).

In particular, the HiSeq® 2500 sequencer was used to sequence a "DNA_Nexus_hiseq2500" sample, the HiSeq® X sequencer was used to sequencer a "DNA_Nexus_hiseqX" sample, and a NovaSeq® sequencer was used to sequence a "DNA_Nexus_NovaSeq" sample, a "NovaSeq_NA12878_rep1 sample," a "NovaSeq_TruSeq-nano-550 sample," and an "AWS_HG005_40x" sample. The "AWS_HG005_40X" came from the subject HG005. All of the other samples came from the subject HG001.

FIG. 7 is an illustration of a bar graph 700 displaying data representing test results in the form of a percentage of unmapped reads in a system using a flexible seed extension method as described herein compared with a system not using a flexible seed extension method. The bar graph 700 is a graphical representation of test results 710, 720, 730, 740, 750, and 760 comparing results of mapping operations performed on genomic reads generated by different Illumina, Inc. sequencing devices.

In a first example, the test results 710 show that the percentage of unmapped reads that occur **710*b* when a HiSeq® 2500 sequencer sequences the "DNA_Nexus_hiseq2500" sample and utilizes flexible seed extension, as described in one or more implementations herein, during mapping is significantly less than the percentage of unmapped reads that occur 710*a*** when the HiSeq® 2500 sequencer sequences the "DNA_Nexus_hiseq2500" sample without utilizing flexible seed extension, as described in one or more implementations herein, during mapping.

In a second example, the test results 720 show that the percentage of unmapped reads that occur 720*b* when a NovaSeq® sequencer sequences the "DNA_Nexus_NovaSeq" sample and utilizes flexible seed extension, as described in one or more implementations herein, during mapping is significantly less than the percentage of unmapped reads that occur 720*a* when the NovaSeq® sequencer sequences the "DNA_Nexus_NovaSeq" sample without utilizing flexible seed extension, as described in one or more implementations herein, during mapping.

In a third example, the test results 730 show that the percentage of unmapped reads that occur 730*b* when a HiSeq® X sequencer sequences the "DNA_Nexus_hiseqX" sample and utilizes flexible seed extension, as described in one or more implementations herein, during mapping is significantly less than the percentage of unmapped reads that occur 730*a* when the HiSeq® X sequencer sequences the "DNA_Nexus_hiseqX" sample without utilizing flexible seed extension, as described in one or more implementations herein, during mapping.

In a fourth example, the test results 740 show that the percentage of unmapped reads that occur 740*b* when a NovaSeq® sequencer sequences the "NovaSeq_NA12878_rep1" sample and utilizes flexible seed extension, as described in one or more implementations herein, during mapping is significantly less than the percentage of unmapped reads that occur 740*a* when the NovaSeq® sequencer sequences the "NovaSeq_NA12878_rep1" sample without utilizing flexible seed extension, as described in one or more implementations herein, during mapping.

In a fifth example, the test results 750 show that the percentage of unmapped reads that occur 750*b* when a NovaSeq® sequencer sequences the "NovaSeq_TruSeq-nano-550" sample and utilizes flexible seed extension, as described in one or more implementations herein, during mapping is significantly less than the percentage of unmapped reads that occur 750*a* when the NovaSeq® sequencer sequences the "NovaSeq_TruSeq-nano-550" sample without utilizing flexible seed extension, as described in one or more implementations herein, during mapping.

In a sixth example, the test results 760 show that the percentage of unmapped reads that occur 760*b* when a NovaSeq® sequencer sequences the "AWS_HG005_40X" sample and utilizes flexible seed extension, as described in one or more implementations herein, during mapping is significantly less than the percentage of unmapped reads that occur 760*a* when the NovaSeq® sequencer sequences the "AWS_HG005_40X" sample without utilizing flexible seed extension, as described in one or more implementations herein, during mapping.

Thus, implementation of flexible seed extension that uses the hash tables described herein achieves significant performance improvements in terms of reducing unmapped reads when compare to conventional methods that do not generate or use the hash tables described herein.

Example 2: Comparing Read Mapping Accuracy Between Systems that Use Flexible Seed Extension and Systems that do not Use Flexible Seed Extension In this example, a DRAGEN™ platform was used to map reads generated by a nucleic acid sequencer to a reference sequence. Each DRAGEN™ platform mapped the same set of reads to the same reference sequencer. Once mapping was completed, a computer system determined a read mapping accuracy for each mapping operation as a function of the mapping error rate.

The DRAGEN™ platform is a mapping and alignment unit implemented in hardware circuitry of a field programmable gate array (FPGA). The DRAGEN™ v7 platform does not currently utilize flexible seed extension, as described in here, whereas the DRAGEN™ v8 platform and the DRAGEN™ v8 hi-effort platform do utilize flexible seed extension.

Although DRAGEN™ platforms used herein were implemented in an FPGA, in general, DRAGEN™ platforms can also be implemented in other integrated circuits, such as an application specific integrated circuit (ASIC).

The difference between the DRAGEN™ v8 platform and the DRAGEN™ v8 hi-effort platform is the setting of heuristics and other parameters. The DRAGEN™ v8 platform uses the following heuristics: intvl-target-hits=32, intvl-max-hits=16, and intvl-sample-hits=16. Each of these heuristics is described herein. In addition, the DRAGEN™ v8 platform uses other parameters of max-hifreq-hits=16, rescue-hifreq=0, and sw-extra-intv1=1. The max-hifreq-hits parameter indicates a maximum number of random sample matches taken from match intervals reached prior to failed seed extension (e.g., one sample per failed extension, until the limit is reached). The rescue-hifreq parameter determines whether expensive rescue scan operations are utilized for matches found only by random samples from match intervals. Rescue scans are a method for searching for possible mate read alignments nearby candidate read alignments. The sw-extra-intvl parameter determines a policy for utilizing expensive Smith-Waterman alignment for matches found by accessing a best ("extra") interval, or found by randomly sampling a match interval. Smith-Waterman is generally not used when gapless alignments are unclipped, but may be employed when gapless alignments are clipped, depending on heuristics including this setting. A setting of "1" means Smith-Waterman may be used for candidates from extra/best match intervals which are accessed in their entirety, but not by random sampling. A setting of "2" means Smith-Waterman may also be used for candidates from random sampling of match intervals. A setting of "0" would mean Smith-Waterman is not applied for candidates from extra/best interval processing or from random sampling of match intervals.

On the other hand, the DRAGEN™ v8 hi-effort platform uses the following heuristics: intvl-target-hits=32, intvl-max-hits=64, and intvl-sample-hits=48. In addition, the DRAGEN™ v8 hi-effort platform uses other parameters of max-hifreq-hits=32, rescue-hifreq=0, and sw-extra-intvl=2. Accordingly, the DRAGEN™ v8 hi-effort platform has a more generous set of heuristics than the DRAGEN™ v8 platform.

Figure 8:
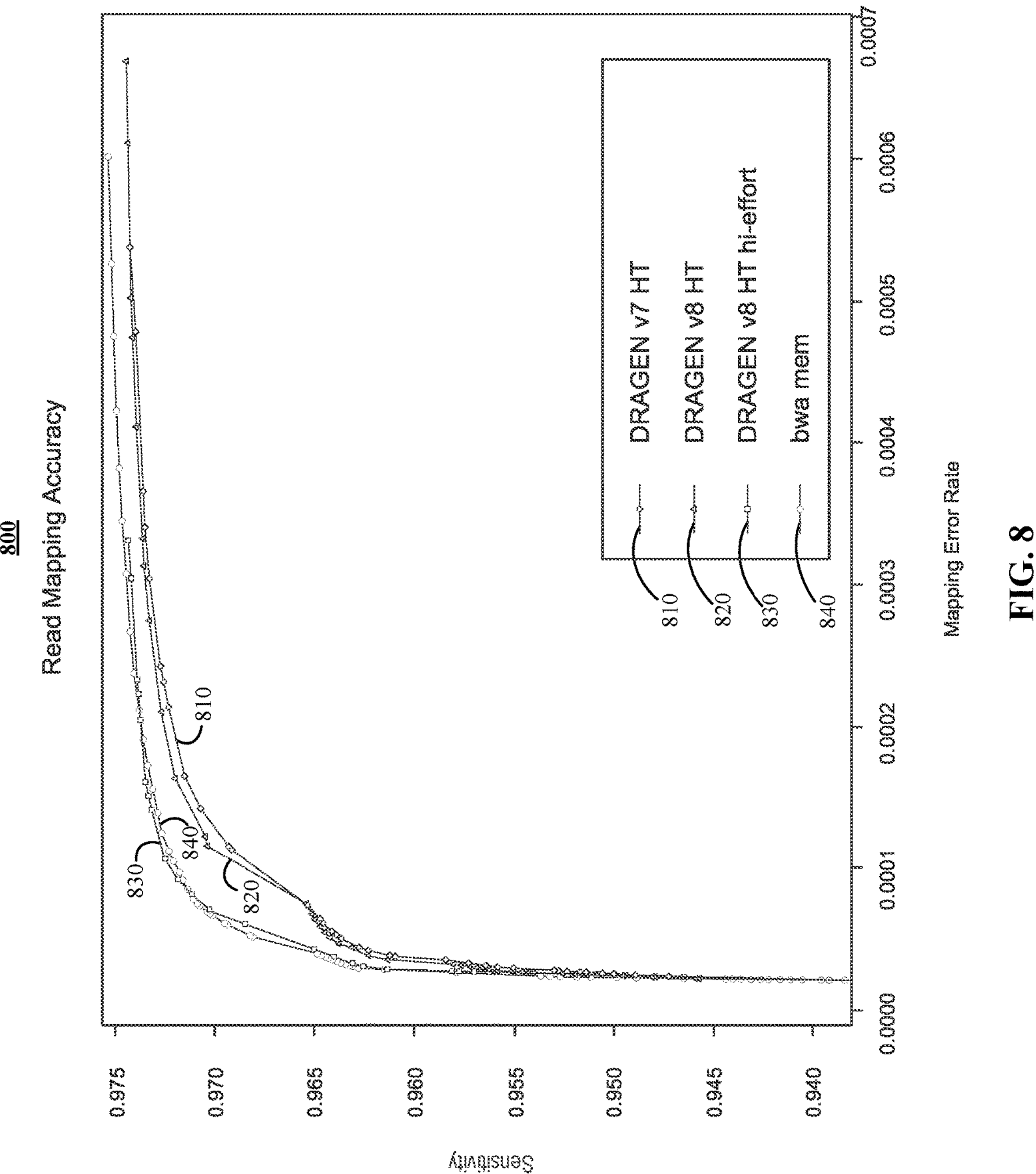
FIG. 8 is an illustration of a line graph displaying data representing test results in the form of read mapping accuracy in a system using a flexible seed extension method as disclosed herein compared with a system not using a flexible seed extension method.

FIG. 8 is an illustration of a line graph 800 displaying data representing test results in the form of read mapping accuracy in a system using a flexible seed extension method as disclosed herein compared with a system not using a flexible seed extension method. In particular, the graph 800 uses an accuracy curve in the form of a receiver operating characteristic ("ROC") curve (or line) to show the tradeoff between false positives and false negatives when the data is stratified using a confidence metric. In illustration of FIG. 8, a curve (or line) closer to the top and left walls of the graph 800 imply better read mapping accuracy.

The curve 810 is depicted that represents read mapping accuracy for the DRAGEN™ v7 platform that does not use flexible seed extension, as described in one or more implementations herein, during mapping. The curve 820 is depicted that represents read mapping accuracy for the DRAGEN™ v8 platform that uses flexible seed extension, as described in one or more implementations herein, during mapping. A comparison of curve 810 and curve 820 reveals that the curve 820 is closer to the top and left walls than the curve 810. Thus, improvements in read mapping accuracy have been achieved merely by implementing flexible seed extension in some capacity, as described in one or more implementations herein.

FIG. 8 further depicts curve 830, which represents a DRAGEN™ implementation v8 with "hi-effort." Like the DRAGEN™ v8 implementation, the DRAGEN™ v8 hi-effort implementation also employs a flexible seed extension method, as described herein, during mapping. However, as described above, the heuristics employed by the DRAGEN™ v8 "hi-effort" implementation are more generous than the heuristics used to employ the DRAGEN™ v8 implementations whose performance is represented by the 820 curve. The "hi-effort" v8 version of DRAGEN™ is assigned a parameter (e.g., sw-extra-intvl=2) that increases a willingness to perform more Smith-Waterman alignment work downstream relative to the DRAGEN™ v8 implementation (e.g., sw-extra-intvl=1). As shown by FIG. 8, the curve 830 is closer to the top and left walls than both of curves 810 and 820, thereby exhibiting significant performance gains in read mapping accuracy by the DRAGEN™ v8 h-effort implementation.

FIG. 8 also depicts a curve 840 that represents a read mapping accuracy achieved by a BWA-MEM software mapping tool. The BWA-MEM software mapping tool uses a Burrows-Wheeler Transform (BWT) of a reference genome as its index. This method of representing a reference genome can inherently provide benefits similar to those offered by flexible seed extension such as the ability to retrieve the full set of matches corresponding to any length of match. As depicted by the curves 830 and 840, the DRAGEN™ v8 "hi-effort" implementation can achieve the same read mapping accuracy as the software-based BWA software mapping tool. It is thus significant for DRAGEN™ v8 "hi-effort" to be able to achieve comparable read mapping accuracy level as the software-based BWA mapping tool because DRAGEN™ v8 "hi-effort" also avails itself of other benefits of the DRAGEN™ platform that include, for example, fewer memory accesses to map seeds. However, prior to the implementation of hardware based flexible seed extension described herein, the DRAGEN™ platform was able to achieve the same levels of read mapping accuracy as those achieved by the BWA software mapping tool.

Thus, implementation of flexible seed extension that uses the hash tables described herein achieves significant performance improvements in terms of read mapping accuracy when compare to conventional methods that do not generate or use the hash tables described herein.

Other Embodiments

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A method for using a hash table to improve the mapping of sample reads to a reference sequence, the method comprising:

executing, by a mapping and aligning unit, a query of a hash table, the query including a first seed, wherein the first seed includes a subset of nucleotides that were obtained from a particular read of the sample reads;

obtaining, by the mapping and aligning unit, a response to the executed query that includes information stored by a location of the hash table that is determined to be responsive to the query;

determining, by the mapping and aligning unit, whether the response to the executed query includes (i) an extend record and (ii) an interval record, wherein the interval record identifies a contiguous set of reference sequence locations, stored in an extension table, that match the first seed;

based on determining, by the mapping and aligning unit, that the response to the executed query includes (i) an extend record and (ii) an interval record:

determining, by the mapping and aligning unit, whether the extension table is to be accessed to obtain one or more matching reference sequence locations in the extension table that are referenced by the interval record; and based on determining that the extension table is to be accessed:

accessing, by the mapping and aligning unit, the extension table to obtain the one or more matching reference sequence locations in the extension table that are referenced by the interval record; and adding, by the mapping and aligning unit, the one or more matching reference sequence locations to a seed match set.

2. The method of claim 1, the method further comprising:

based on determining that the extension table is not to be accessed:

determining, by the mapping and aligning unit, whether to store the first information describing the interval record in a memory device as information describing a candidate best interval;

generating, by the mapping and aligning unit, a first extended seed that is an extension of the first seed using the extend record;

generating, by the mapping and aligning unit, a subsequent hash query that includes the first extended seed; and executing, by the mapping and aligning unit, the subsequent hash query of the hash table.

3. The method of claim 2, the method further comprising:

determining, by the mapping and aligning unit, that the response to the executed query includes one or more matching reference sequence locations; and based on determining, by the mapping and aligning unit, that the response to the executed query includes one or more matching reference sequence locations:

adding, by the mapping and aligning unit, the one or more matching reference sequence locations to a seed match set.

4. The method of claim 2, wherein determining, by the mapping and aligning unit, whether to store the first information describing the interval record in a memory device as information describing a candidate best interval comprises:

determining, by the mapping and aligning unit, that there is not prior information describing an interval record as a candidate best interval for the particular read; and storing, by the mapping and aligning unit, the first information describing the interval record in the memory device as information describing a candidate best interval.

5. The method of claim 2, the method further comprising:

obtaining, by the mapping and aligning unit, a response to the subsequent executed query that includes information stored by a location of the hash table that is determined to be responsive to the query;

determining, by the mapping and aligning unit, whether the response to the subsequent executed query includes (i) a second extend record (ii) a second interval record, and (iii) one or more matching reference sequence locations;

based on determining, by the mapping and aligning unit, that the response to the subsequent executed query includes (i) the second extend record and (ii) the second interval record:

determining, by the mapping and aligning unit, whether the extension table is to be accessed to obtain one or more matching reference sequence locations in the extension table that are referenced by the second interval record;

based on determining that the extension table is not to be accessed:

determining, by the mapping and aligning unit and using one or more heuristic rules, whether second information describing the second interval record or the first information describing the candidate best interval is to be used as the candidate best interval;

generating, by the mapping and aligning unit, a second extended seed that is an extension of the first extended seed using the second extend record;

generating, by the mapping and aligning unit, a third hash query that includes the second extended seed; and executing, by the mapping and aligning unit, the third query of the hash table that includes the second extended seed.

6. The method of claim 5, wherein determining, by the mapping and aligning unit and using one or more heuristic rules, whether the second information describing the second interval record or the first information describing the candidate best interval is to be used as the best interval comprises:

selecting either the second information describing the second interval record or the first information describing the candidate best interval record based on a plurality of factors that include (i) a number of matching reference sequence locations returned by each of the interval record and the second interval record, (ii) a predetermined threshold level of reference sequence locations, or (iii) each seed length of the respective seeds that reached the hash locations storing the interval record and the second interval record.

7. A system for using a hash table to improve the mapping of sample reads to a reference sequence comprising:

one or more computers and one or more storage devices storing instructions that are operable, when executed by the one or more computers, to cause the one or more computers to perform operations comprising:

executing, by a mapping and aligning unit, a query of a hash table, the query including a first seed, wherein the first seed includes a subset of nucleotides that were obtained from a particular read of the sample reads;

obtaining, by the mapping and aligning unit, a response to the executed query that includes information stored by a location of the hash table that is determined to be responsive to the query;

determining, by the mapping and aligning unit, whether the response to the executed query includes (i) an extend record and (ii) an interval record, wherein the interval record identifies a contiguous set of reference sequence locations, stored in an extension table, that match the first seed;

based on determining, by the mapping and aligning unit, that the response to the executed query includes (i) an extend record and (ii) an interval record:

determining, by the mapping and aligning unit, whether the extension table is to be accessed to obtain one or more matching reference sequence locations in the extension table that are referenced by the interval record; and based on determining that the extension table is to be accessed:

accessing, by the mapping and aligning unit, the extension table to obtain the one or more matching reference sequence locations in the extension table that are referenced by the interval record; and adding, by the mapping and aligning unit, the one or more matching reference sequence locations to a seed match set.

8. The system of claim 7, the operations further comprising:

based on determining that the extension table is not to be accessed:

determining, by the mapping and aligning unit, whether to store the first information describing the interval record in a memory device as information describing a candidate best interval;

generating, by the mapping and aligning unit, a first extended seed that is an extension of the first seed using the extend record;

generating, by the mapping and aligning unit, a subsequent hash query that includes the first extended seed; and executing, by the mapping and aligning unit, the subsequent hash query of the hash table.

9. The system of claim 8, the operations further comprising:

determining, by the mapping and aligning unit, that the response to the executed query includes one or more matching reference sequence locations; and based on determining, by the mapping and aligning unit, that the response to the executed query includes one or more matching reference sequence locations:

adding, by the mapping and aligning unit, the one or more matching reference sequence locations to a seed match set.

10. The system of claim 8, wherein determining, by the mapping and aligning unit, whether to store the first information describing the interval record in a memory device as information describing a candidate best interval comprises:

determining, by the mapping and aligning unit, that there is not prior information describing an interval record as a candidate best interval for the particular read; and storing, by the mapping and aligning unit, the first information describing the interval record in the memory device as information describing a candidate best interval.

11. The system of claim 8, the operations further comprising:

obtaining, by the mapping and aligning unit, a response to the subsequent executed query that includes information stored by a location of the hash table that is determined to be responsive to the query;

determining, by the mapping and aligning unit, whether the response to the subsequent executed query includes (i) a second extend record (ii) a second interval record, and (iii) one or more matching reference sequence locations;

based on determining, by the mapping and aligning unit, that the response to the subsequent executed query includes (i) the second extend record and (ii) the second interval record:

determining, by the mapping and aligning unit, whether the extension table is to be accessed to obtain one or more matching reference sequence locations in the extension table that are referenced by the second interval record;

based on determining that the extension table is not to be accessed:

determining, by the mapping and aligning unit and using one or more heuristic rules, whether second information describing the second interval record or the first information describing the candidate best interval is to be used as the candidate best interval;

generating, by the mapping and aligning unit, a second extended seed that is an extension of the first extended seed using the second extend record;

generating, by the mapping and aligning unit, a third hash query that includes the second extended seed; and executing, by the mapping and aligning unit, the third query of the hash table that includes the second extended seed.

12. The system of claim 11, wherein determining, by the mapping and aligning unit and using one or more heuristic rules, whether the second information describing the second interval record or the first information describing the candidate best interval is to be used as the best interval comprises:

selecting either the second information describing the second interval record or the first information describing the candidate best interval record based on a plurality of factors that include (i) a number of matching reference sequence locations returned by each of the interval record and the second interval record, (ii) a predetermined threshold level of reference sequence locations, or (iii) each seed length of the respective seeds that reached the hash locations storing the interval record and the second interval record.

13. The system of claim 7, wherein the interval record references one or more locations, in the seed extension table, that include data describing reference sequence locations that match the first seed of the query.

14. The system of claim 13, wherein the one or more locations, in the seed extension table, that include data describing reference sequence locations that match the first seed of the query comprises:

a contiguous interval, in an extension table, of reference sequence locations that match the first seed of the query.

15. A non-transitory, computer-readable medium storing software comprising instructions executable by one or more computers which, upon such execution, cause the one or more computers to perform operations comprising:

executing, by a mapping and aligning unit, a query of a hash table, the query including a first seed, wherein the first seed includes a subset of nucleotides that were obtained from a particular read of the sample reads;

obtaining, by the mapping and aligning unit, a response to the executed query that includes information stored by a location of the hash table that is determined to be responsive to the query;

determining, by the mapping and aligning unit, whether the response to the executed query includes (i) an extend record and (ii) an interval record, wherein the interval record identifies a contiguous set of reference sequence locations, stored in an extension table, that match the first seed;

based on determining, by the mapping and aligning unit, that the response to the executed query includes (i) an extend record and (ii) an interval record:

determining, by the mapping and aligning unit, whether an extension table is to be accessed to obtain one or more matching reference sequence locations in the extension table that are referenced by the interval record;

based on determining that the extension table is to be accessed:

accessing, by the mapping and aligning unit, the extension table to obtain the one or more matching reference sequence locations in the extension table that are referenced by the interval record; and adding, by the mapping and aligning unit, the one or more matching reference sequence locations to a seed match set.

16. The computer-readable medium of claim 15, the operations further comprising:

based on determining that the extension table is not to be accessed:

determining, by the mapping and aligning unit, whether to store the first information describing the interval record in a memory device as information describing a candidate best interval;

generating, by the mapping and aligning unit, a first extended seed that is an extension of the first seed using the extend record;

generating, by the mapping and aligning unit, a subsequent hash query that includes the first extended seed; and executing, by the mapping and aligning unit, the subsequent hash query of the hash table.

17. The computer-readable medium of claim 16, the operations further comprising:

determining, by the mapping and aligning unit, that the response to the executed query includes one or more matching reference sequence locations; and based on determining, by the mapping and aligning unit, that the response to the executed query includes one or more matching reference sequence locations:

adding, by the mapping and aligning unit, the one or more matching reference sequence locations to a seed match set.

18. The computer-readable medium of claim 16, wherein determining, by the mapping and aligning unit, whether to store the first information describing the interval record in a memory device as information describing a candidate best interval comprises:

determining, by the mapping and aligning unit, that there is not prior information describing an interval record as a candidate best interval for the particular read; and storing, by the mapping and aligning unit, the first information describing the interval record in the memory device as information describing a candidate best interval.

19. The computer-readable medium of claim 16, the operations further comprising:

obtaining, by the mapping and aligning unit, a response to the subsequent executed query that includes information stored by a location of the hash table that is determined to be responsive to the query;

determining, by the mapping and aligning unit, whether the response to the subsequent executed query includes (i) a second extend record (ii) a second interval record, or (iii) one or more matching reference sequence locations;

based on determining, by the mapping and aligning unit, that the response to the subsequent executed query includes (i) the second extend record and (ii) the second interval record:

determining, by the mapping and aligning unit, whether the extension table is to be accessed to obtain one or more matching reference sequence locations in the extension table that are referenced by the second interval record;

based on determining that the extension table is not to be accessed:

determining, by the mapping and aligning unit and using one or more heuristic rules, whether second information describing the second interval record or the first information describing the candidate best interval is to be used as the candidate best interval;

generating, by the mapping and aligning unit, a second extended seed that is an extension of the first extended seed using the second extend record;

generating, by the mapping and aligning unit, a third hash query that includes the second extended seed; and executing, by the mapping and aligning unit, the third query of the hash table that includes the second extended seed.

20. The computer-readable medium of claim 19, wherein determining, by the mapping and aligning unit and using one or more heuristic rules, whether the second information describing the second interval record or the first information describing the candidate best interval is to be used as the best interval comprises:

selecting either the second information describing the second interval record or the first information describing the candidate best interval record based on a plurality of factors that include (i) a number of matching reference sequence locations returned by each of the interval record and the second interval record, (ii) a predetermined threshold level of reference sequence locations, or (iii) each seed length of the respective seeds that reached the hash locations storing the interval record and the second interval record.

21. An integrated circuit for using a hash table to improve the mapping of sample reads to a reference sequence, the integrated circuit comprising multiple hardware logic gates that have been physically configured into one or more hardware digital logic circuits that realize functionality of a mapping and aligning unit, the integrated circuit comprising:

one or more hardware logic circuits that execute a query of a hash table, the query including a first seed, wherein the first seed includes a subset of nucleotides that were obtained from a particular read of the sample reads;

one or more hardware logic circuits that obtain a response to the executed query that includes information stored by a location of the hash table that is determined to be responsive to the query;

one or more hardware logic circuits that determine whether the response to the executed query includes (i) an extend record and (ii) an interval record, wherein the interval record identifies a contiguous set of reference sequence locations, stored in an extension table, that match the first seed;

one or more hardware logic circuits that, based on a determination that the response to the executed query includes (i) an extend record and (ii) an interval record, determine whether the extension table is to be accessed to obtain one or more matching reference sequence locations in the extension table that are referenced by the interval record; and one or more hardware logic circuits that, based on determining that the extension table is to be accessed: accessing the extension table to obtain the one or more matching reference sequence locations in the extension table that are referenced by the interval record, and adding the one or more matching reference sequence locations to a seed match set.

22. The integrated circuit of claim 21, wherein the integrated circuit is a field programmable gate array (FPGA).

* * * * *